United States Patent
Chase et al.

(10) Patent No.: US 10,214,539 B2
(45) Date of Patent: *Feb. 26, 2019

(54) INTERMEDIATES AND METHODS FOR THE SYNTHESIS OF HALICHONDRIN B ANALOGS

(71) Applicant: EISAI R&D MANAGEMENT CO., LTD., Tokyo (JP)

(72) Inventors: Charles E. Chase, Londonderry, NH (US); Atsushi Endo, Boston, MA (US); Francis G. Fang, Andover, MA (US); Jing Li, Andover, MA (US)

(73) Assignee: EISAI R&D MANAGEMENT CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/787,268

(22) Filed: Oct. 18, 2017

(65) Prior Publication Data
US 2018/0037588 A1     Feb. 8, 2018

Related U.S. Application Data

(60) Continuation of application No. 15/092,850, filed on Apr. 7, 2016, now Pat. No. 9,802,953, which is a division of application No. 14/624,033, filed on Feb. 17, 2015, now Pat. No. 9,604,993, which is a continuation of application No. 13/334,516, filed on Dec. 22, 2011, now Pat. No. 8,987,479, which is a continuation of application No. 12/245,149, filed on Oct. 3, 2008, now Pat. No. 8,093,410.

(60) Provisional application No. 60/997,625, filed on Oct. 3, 2007.

(51) Int. Cl.
| | | |
|---|---|---|
| C07D 493/20 | (2006.01) |
| C07D 307/28 | (2006.01) |
| C07D 307/33 | (2006.01) |
| C07D 493/08 | (2006.01) |
| C07D 493/18 | (2006.01) |
| C07D 493/04 | (2006.01) |
| C07D 493/22 | (2006.01) |
| C07D 307/20 | (2006.01) |
| C07D 307/26 | (2006.01) |
| C07D 309/16 | (2006.01) |
| C07D 405/06 | (2006.01) |
| C07D 405/14 | (2006.01) |

(52) U.S. Cl.
CPC ......... *C07D 493/20* (2013.01); *C07D 307/20* (2013.01); *C07D 307/26* (2013.01); *C07D 307/28* (2013.01); *C07D 307/33* (2013.01); *C07D 309/16* (2013.01); *C07D 405/06* (2013.01); *C07D 405/14* (2013.01); *C07D 493/04* (2013.01); *C07D 493/08* (2013.01); *C07D 493/18* (2013.01); *C07D 493/22* (2013.01); *Y02P 20/55* (2015.11)

(58) Field of Classification Search
CPC .................................................. C07D 493/20
See application file for complete search history.

(56) References Cited

U.S. PATENT DOCUMENTS

| | | |
|---|---|---|
| 5,338,865 A | 8/1994 | Kishi et al. |
| 5,436,238 A | 7/1995 | Kishi et al. |
| 5,451,573 A | 9/1995 | Hemmerle et al. |
| 6,194,586 B1 | 2/2001 | Martinelli et al. |
| 6,214,865 B1 | 4/2001 | Littlefield et al. |
| 6,365,759 B1 | 4/2002 | Littlefield et al. |
| 6,469,182 B1 | 10/2002 | Littlefield et al. |
| 6,653,341 B1 | 11/2003 | Littlefield et al. |
| 7,470,720 B2 | 12/2008 | Littlefield et al. |
| 7,982,060 B2 | 7/2011 | Austad et al. |
| 8,093,410 B2 | 1/2012 | Chase et al. |
| 8,097,648 B2 | 1/2012 | Littlefield et al. |
| 8,148,554 B2 | 4/2012 | Seletsky et al. |
| 8,203,010 B2 | 6/2012 | Endo et al. |
| 8,350,067 B2 | 1/2013 | Endo et al. |
| 8,445,701 B2 | 5/2013 | Austad et al. |
| 8,598,373 B2 | 12/2013 | Hu |
| 8,618,313 B2 | 12/2013 | Benayoud et al. |
| 8,884,031 B2 | 11/2014 | Chase et al. |
| RE45,324 E | 1/2015 | Austad et al. |
| 8,927,597 B2 | 1/2015 | Endo et al. |
| 8,975,422 B2 | 3/2015 | Fang et al. |
| 8,987,479 B2 | 3/2015 | Chase et al. |
| 9,206,194 B2 | 12/2015 | Hu |
| 9,303,039 B2 | 4/2016 | Zhang et al. |
| 9,303,050 B2 | 4/2016 | Benayoud et al. |
| 9,382,262 B2 | 7/2016 | Endo et al. |
| 9,469,651 B2 | 10/2016 | Hu |
| 9,604,993 B2 | 3/2017 | Chase et al. |
| 9,695,188 B2 | 7/2017 | Hu et al. |
| 9,783,549 B2 | 10/2017 | Fang et al. |
| 9,802,953 B2 | 10/2017 | Chase et al. |
| 9,856,276 B2 | 1/2018 | Endo et al. |

(Continued)

FOREIGN PATENT DOCUMENTS

| | | |
|---|---|---|
| EP | 0572109 A1 | 12/1993 |
| JP | H06-211737 A | 8/1994 |

(Continued)

OTHER PUBLICATIONS

U.S. Appl. No. 13/924,892, Austad et al.

(Continued)

*Primary Examiner* — Golam M Shameem
(74) *Attorney, Agent, or Firm* — Clark & Elbing LLP

(57) ABSTRACT

Methods of synthesizing intermediates useful for the synthesis of halichondrin B analogs are described.

4 Claims, No Drawings

(56) References Cited

U.S. PATENT DOCUMENTS

| | | |
|---|---|---|
| 2006/0045846 A1 | 3/2006 | Horstmann et al. |
| 2007/0244187 A1 | 10/2007 | Austad et al. |
| 2009/0198074 A1 | 8/2009 | Chase et al. |
| 2009/0203771 A1 | 8/2009 | Inanaga et al. |
| 2011/0054194 A1 | 3/2011 | Hu |
| 2011/0172446 A1 | 7/2011 | Littlefield et al. |
| 2011/0184190 A1 | 7/2011 | Endo et al. |
| 2012/0029213 A1 | 2/2012 | Austad et al. |
| 2012/0309988 A1 | 12/2012 | Austad et al. |
| 2013/0123519 A1 | 5/2013 | Endo et al. |
| 2013/0237711 A1 | 9/2013 | Benayoud et al. |
| 2015/0158881 A1 | 6/2015 | Hu et al. |
| 2015/0175620 A1 | 6/2015 | Endo et al. |
| 2015/0225415 A1 | 8/2015 | Chase et al. |
| 2015/0232490 A1 | 8/2015 | Benayoud et al. |
| 2015/0315206 A1 | 11/2015 | Hu |
| 2016/0176895 A1 | 6/2016 | Hu et al. |
| 2016/0264594 A1 | 9/2016 | Fang et al. |
| 2016/0376294 A1 | 12/2016 | Endo et al. |
| 2017/0298078 A1 | 10/2017 | Hu et al. |
| 2018/0002342 A1 | 1/2018 | Fang et al. |
| 2018/0118755 A1 | 5/2018 | Fang et al. |
| 2018/0162885 A1 | 6/2018 | Endo et al. |

FOREIGN PATENT DOCUMENTS

| | | |
|---|---|---|
| SU | 652180 A1 | 3/1979 |
| WO | WO-93/17690 A1 | 9/1993 |
| WO | WO-99/65894 A1 | 12/1999 |
| WO | WO-2005/118565 A1 | 12/2005 |
| WO | WO-2006/076100 A2 | 7/2006 |
| WO | WO-2008/010776 A1 | 1/2008 |
| WO | WO-2009/064029 A1 | 5/2009 |
| WO | WO-2009/124237 A1 | 10/2009 |
| WO | WO-2011/094339 A1 | 8/2011 |
| WO | WO-2012/147900 A1 | 11/2012 |
| WO | WO-2013/078559 A1 | 6/2013 |
| WO | WO-2013/142999 A1 | 10/2013 |
| WO | WO-2015/066729 A1 | 5/2015 |
| WO | WO-2016/179607 A1 | 11/2016 |
| WO | WO-2017/139664 | 8/2017 |
| WO | WO-2018/006031 | 1/2018 |

OTHER PUBLICATIONS

U.S. Appl. No. 15/571,921, filed Nov. 6, 2017, Hu et al.

U.S. Appl. No. 15/840,109, filed Dec. 13, 2017, Endo et al.

Aicher et al., "Synthetic studies towards halichondrins: synthesis of the C.27-C.38 segment," Tetrahedron Lett. 33(12):1549-52 (1992).

Aicher et al., "Total synthesis of halichondrin B and norhalichondrin B," J Am Chem Soc. 114(8):3162-4 (1992).

Aicher, Thomas Daniel, Thesis, Chapter 4, "Synthetic studies towards halichondrin B," Doctor of Philosophy in Chemistry, Harvard University, 35-54, 1989 (26 pages).

Alley et al. "Comparison of the relative efficacies and toxicities of Halichondrin B analogues," Proceedings of the AACR-NCI-EORTC Conference on Molecular Targets and Cancer Therapeutics. C230:257 (2005).

Anderson, "Developing processes for crystallization-induced asymmetric transformation," Org Process Res Dev. 9:800-13 (2005).

Austad et al. (2005): STN International HCAPLUS database, Columbus (OH), accession No. 2005: 1313925.

Austad et al., "Commercial manufacture of Halaven®: chemoselective transformations en route to structurally complex macrocyclic ketones," Synlett. 24 (2013). Supporting Information, (13 pages.).

Austad et al., "Commercial manufacture of Halaven®: chemoselective transformations en route to structurally complex macrocyclic ketones," Synlett. 24(3):333-7 (2013).

Austad et al., "Process development of Halaven®: synthesis of the C14-C35 fragment via iterative Nozaki-Hiyama-Kishi reaction—Williamson ether cyclization," Synlett. 24(3):327-32 (2013).

Bai et al., "Halichondrin B and Homohalichondrin B, marine natural products binding in the vinca domain of tubulin. Discovery of tubulin-based mechanism of action by analysis of differential cytotoxicity data," J Biol Chem. 266(24):15882-9 (1991).

Bernet et al., "Carbocyclische verbindungen aus monosacchariden. I. Umsetzungen in der glucosereihe," Helv Chim Acta. 62(6):1990-2016 (1979).

Blanchette et al., "Horner-Wadsworth-Emmons reaction: use of lithium chloride and an amine for base-sensitive compounds," Tetrahedron Lett. 25(21):2183-6 (1984).

Burke et al., "Enantioselective synthesis of a Halichondrin B C(20) → C(36) precursor," Tetrahedron Lett. 36(39):7023-6 (1995).

Burke et al., "Synthesis of a C(22)-C(34) Halichondrin B precursor via ring opening-double ring closing metathesis," J Org Chem. 63:8626-7 (1998).

Burke et al., "Synthesis of a C(22) → C(34) Halichondrin precursor via a double dioxanone-to-dihydropyran rearrangement," Tetrahedron Lett. 32(32):3961-4 (1991).

Burke et al., "Synthetic studies toward complex polyether macrolides of marine origin," Spec Publ R Soc Chem. 198:(Anti-Infectives) 73-85 (1997).

Chase et al., "Process development of Halaven®: Synthesis of the C1-C13 fragment from D-(−)-Gulono-1,4-lactone," Synlett. 24(3):323-6 (2013).

Chen et al., "Ni(II)/Cr(II)-mediated coupling reaction: An asymmetric process," J Org Chem. 60(17):5386-7 (1995).

Choi et al., "Asymmetric Ni(II)/Cr(II)-mediated coupling reaction: catalytic process," Org Lett. 4(25):4435-8 (2002).

Choi et al., "Supporting information for asymmetric Ni(II)/Cr(II)-mediated coupling reaction: catalytic process," Org Lett. 4(25) (2002) (8 pages).

Choi et al., "Synthetic studies on the marine natural product Halichondrins," Pure Appl Chem. 75(1):1-17 (2003).

Cooper et al., "Total Synthesis of Halichondrin B from common sugars: an F-ring intermediate from D-glucose and efficient construction of the C1 to C21 segment," Tetrahedron Lett. 34(51):8193-6 (1993).

Dabydeen et al. "Comparison of the activities of the truncated Halichondrin B analog NSC 707389 (E7389) with those of the parent compound and a proposed binding site on tubulin," Mol Pharmacol. 70(6):1866-75 (2006).

Dong et al. "New syntheses of E7389 C14-C35 and halichondrin C14-C38 building blocks: reductive cyclization and oxy-michael cyclization approaches," J Am Chem Soc. 131(43):15642-6 (2009).

Duan et al., "Synthetic studies on halichondrins: a new practical synthesis of the C.1-C.12 segment," Tetrahedron Lett. 34(47):7541-4 (1993).

Fleming et al., "Nitrile anion cyclizations," Tetrahedron. 58(1):1-23 (2002).

Guo et al., "Toolbox approach to the search for effective ligands for catalytic asymmetric Cr-mediated coupling reactions," J Am Chem Soc. 131(42):15387-93 (2009).

Hirata et al., "Halichondrins—antitumor polyether macrolides from a marine sponge," Pure Appl Chem. 58(5):701-10 (1986).

Hori et al., "Efficient synthesis of 2,3-trans-tetrahydropyrans and oxepanes: rearrangement-ring expansion of cyclic ethers having a chloromethanesulfonate," Tetrahedron Lett. 40(11):2145-8 (1999).

Horita et al., "Research on anti-tumor active site of marine source natural product, Halichondrin B.," International Congress Series, 1157 (Towards Natural Medicine Research in the 21st Century), 327-336 (1998).

Horita et al., "Synthetic studies of halichondrin B, an antitumor polyether macrolide isolated from a marine sponge. 2. Efficient synthesis of C16-C26 fragments via construction of the D ring by a highly stereocontrolled iodoetherification," Synlett. 40-43 (1994).

Horita et al., "Synthetic studies of Halichondrin B, an antitumor polyether macrolide isolated from a marine sponge. 3. Synthesis of C27-C36 subunit via completely stereoselective C-glycosylation to the F ring," Synlett. 43-45 (1994).

Horita et al., "Synthetic studies of Halichondrin B, an antitumor polyether macrolide isolated from a marine sponge. 7. Synthesis of two C27-C36 units via construction of the F ring and completely

(56) References Cited

OTHER PUBLICATIONS stereoselective C-glycosylation using mixed Lewis acids," Chem Pharm Bull. 45(10):1558-72 (1997).
Horita et al., "Synthetic studies of Halichondrin B, an antitumor polyether macrolide isolated from a marine sponge. 8. Synthesis of the lactone part (C1-C36) via Horner-Emmons coupling between C1-C15 and C16-C36 fragments and yamaguchi lactonization," Tetrahedron Lett. 38(52):8965-8 (1997).
Horita et al., "Synthetic studies on Halichondrin B, an antitumor polyether macrolide isolated from a marine sponge. 9. Synthesis of the C16-C36 unit via stereoselective construction of the D and E rings," Chem Pharm Bull. 46(8):1199-216 (1998).
Horita et al., Synthetic study of a highly antitumorigenic marine phytochemical, Halichondrin B. *Phytochemicals and Phytopharmaceuticals*. Fereidoon Shahidi and Chi-Tang Ho, 386-397 (2000).
International Preliminary Report on Patentability from International Application No. PCT/US2008/078762, dated Apr. 7, 2010 (7 pages).
International Search Report and Written Opinion from International Application No. PCT/US2008/078762, dated Dec. 3, 2008 (12 pages).
Jackson et al., "A total synthesis of norhalichondrin B," Angew Chem Int Ed. 48(13):2346-50 (2009).
Jackson et al., "The halichondrins and E7389," Chem Rev. 109(7):3044-79 (2009).
Jiang et al. "A novel route to the F-ring of Halichondrin B. Diastereoselection in Pd(0)-mediated meso and C2 diol desymmetrization," Org Lett. 4(20):3411-4 (2002).
Jiang et al., "A practical synthesis of the F-ring of halichondrin B via ozonolytic desymmetrization of a C(2)-symmetric dihydroxycyclohexene," J Org Chem. 68(3):1150-3 (2003).
Kim et al., "New syntheses of E7389 C14-C35 and Halichondrin C14-C38 building blocks: double-inversion approach," J Am Chem Soc. 131(43):15636-41 (2009).
Kurosu et al., "Fe/Cr- and Co/Cr-mediated catalytic asymmetric 2-Haloallylations of aldehydes," J Am Chem Soc. 126(39):12248-9 (2004).
Kurosu et al., "Supporting information for Fe/Cr- and Co/Cr-mediated catalytic asymmetric 2-haloallylations of aldehydes," J Am Chem Soc. 126(39) (2004) (31 pages).
March. *Advanced Organic Chemistry, Fourth Edition*. John Wiley & Sons, 386-388 (1992).
Mattocks, "371. Novel reactions of some alpha-acyloxy acid chlorides," J Chem Soc. Resumed. 1918-30 (1964).
Mattocks, "932. Novel reactions of some alpha-acyloxy-acid halides," J Chem Soc. 4840-5 (1964).
Mitsunobu, "The use of diethyl azodicarboxylate and triphenylphosphine in synthesis and transformation of natural products," Synthesis. 1-28 (1981).
Namba et al., "New catalytic cycle for couplings of aldehydes with organochromium reagents," Org Lett. 6(26):5031-3 (2004).
Newman, "Drug evaluation: eribulin, a simplified ketone analog of the tubulin inhibitor Halichondrin B, for the potential treatment of cancer," Curr Opin Invest Drugs. 8(12):1057-66 (2007).
Sakamoto et al., "Stereoselective ring expansion via bicyclooxonium ion. A novel approach to oxocanes," Org Lett. 4(5):675-8 (2002).
Schreiber, "Hydrogen transfer from tertiary amines to trifluoroacetic anhydride," Tetrahedron Lett. 21(11):1027-30 (1980).
Seletsky et al. "Structurally simplified macrolactone analogues of halichondrin B," Bioorg Med Chem Lett. 14(22):5547-50 (2004).
Stamos et al., "A mild preparation of vinyliodides from vinylsilanes," Tetrahedron Lett. 37(48): 8647-50 (1996).
Stamos et al., "New synthetic route to the C.14-C.38 segment of Halichondrins," J Org Chem. 62(22):7552-3 (1997).
Stamos et al., "Ni(II)/Cr(II)-mediated coupling reaction: beneficial effects of 4-tert-butylpyridine as an additive and development of new and improved workup procedures," Tetrahedron Lett. 38(36):6355-8 (1997).
Stamos et al., "Synthetic studies on Halichondrins: a practical synthesis of the C.1-C.13 segment," Tetrahedron Lett. 37(48):8643-6 (1996).
Sutherland et al., "The synthesis of 6alpha- and 6beta-fluoroshikimic acids," J Chem Soc Chem Commun. 18:1386-7 (1989).
Tokunaga et al., "Asymmetric catalysis with water: efficient kinetic resolution of terminal epoxides by means of catalytic hydrolysis," Science. 277(5328):936-8 (1997).
Towle et al. "Halichondrin B macrocyclic ketone analog E7389: medicinal chemistry repair of lactone ester instability generated during structural simplification to clinical Candidate" Annual Meeting of the American Association for Cancer Research, Apr. 6-10, 2002, 5721 (3 pages).
Towle et al. "In vitro and in vivo anticancer activities of synthetic macrocyclic ketone analogues of Halichondrin B," Cancer Res. 61(3):1013-21 (2001).
Uemura et al., "Norhalichondrin A: an antitumor polyether macrolide from a marine sponge," J Am Chem Soc. 107(16):4796-8 (1985).
Vahdat et al., "Phase II study of eribulin mesylate, a Halichondrin B analog, in patients with metastatic breast cancer previously treated with an anthracycline and a taxane," J Clin Oncol. 27(18):2954-61 (2009).
Varseev et al, "Enantioselective total synthesis of (+)-neosymbioimine," Org Lett. 9(8):1461-4 (2007).
Wan et al., "Asymmetric Ni(II)/Cr(II)-mediated coupling reaction: Stoichiometric process," Org Lett. 4(25):4431-4 (2002) Supporting Information, 8 pages.
Wan et al., "Asymmetric Ni(II)/Cr(II)-mediated coupling reaction: Stoichiometric process," Org Lett. 4(25):4431-4 (2002).
Wang et al., "Facile preparation of peracetates and per-3-bromobenzoates of alpha-mono- and disaccharides," Molecules. 10(10):1325-34 (2005).
Wang et al., "Structure-activity relationships of halichondrin B analogues: modifications at C.30-C.38" Bioorg Med Chem Lett. 10(10):1029-32 (2000).
Xie et al., "Synthesis of the C20-C26 building block of Halichondrins via a regiospecific and stereoselective SN2' reaction," Org Lett. 4(25): 4427-9 (2002).
Yamamoto et al., "Total synthesis of halichondrin C," J Am Chem Soc. 134(2):893-6 (2012).
Yang et al., "Second generation synthesis of C27-C35 building block of E7389, a synthetic Halichondrin analogue," Org Lett. 11(20): 4516-9 (2009).
Youssefyeh, "Acylations of ketals and enol ethers," J Am Chem Soc. 85(23):3901-2 (1963).
Yu et al., "New synthetic route to the C.14-C.21 fragment of Halichondrin B," Book of Abstracts. 219th ACS National Meeting, San Francisco, CA, Mar. 26-30 (2000) (1 page).
Yu et al., Discovery of E7389 a fully synthetic macrocyclic ketone analog of Halichondrin B. *Anticancer Agents from Natural Product*. CRC Press, 241-265 (2005).
Zheng et al., "Macrocyclic ketone analogues of halichondrin B," Bioorg Med Chem Lett. 14(22): 5551-4 (2004).
Zheng et al., "Synthetic macrocyclic ketone analogs of halichondrin B: structure-activity relationships" Proceedings of the American Association for Cancer Research, 41:301, Abstract #1915 (2000).
U.S. Appl. No. 15/944,480, Benayoud et al.
U.S. Appl. No. 10/030,032, filed Jul. 24, 2018, Hu et al.
Ando et al., "Z-selective intramolecular Horner-Wadsworth-Emmons reaction for the synthesis of macrocyclic lactones," Org Lett. 12(7):1460-3 (2010).
Yu et al., "From micrograms to grams: scale-up synthesis of eribulin mesylate," Nat Prod Rep. 30(9):1158-64 (2013).
Yu et al., "Macrocyclic drugs and synthetic methodologies toward macrocycles," Molecules 18(6):6230-68 (2013).

INTERMEDIATES AND METHODS FOR THE SYNTHESIS OF HALICHONDRIN B ANALOGS

This application is a continuation of U.S. application Ser. No. 12/245,149, filed Oct. 3, 2008, which claims priority to U.S. provisional application No. 60/997,625, filed Oct. 3, 2007, the entire contents of which are hereby incorporated herein by reference.

BACKGROUND OF THE INVENTION

The invention relates to a method for the synthesis of halichondrin B and analogs thereof having pharmaceutical activity, such as anticancer or antimitotic (mitosis-blocking) activity. B-1939 (also known as E7389 or eribulin), a halichondrin B analog, has been reported to be useful for treating cancer and other proliferative disorders including melanoma, fibrosarcoma, leukemia, colon carcinoma, ovarian carcinoma, breast carcinoma, osteosarcoma, prostate carcinoma, lung carcinoma, and ras-transformed fibroblasts.

Halichondrin B is a structurally complex marine natural product containing multiple chiral centers on an extended carbon framework. Due to the limited availability of halichondrin B from natural sources, methods for the synthesis of halichondrin B have value for the purposes of developing the full medicinal potential of halichondrin B analogs. A method for the synthesis of halichondrin B analogs was published in 1992 (Aicher, T. D. et al., *J. Am. Chem. Soc.* 114:3162-3164). A method for the synthesis of Halichondrin B analogs, including B-1939, was described in WO 2005/118565 (EISAI COMPANY, LTD.). The method described in WO 2005/118565 has several practical advantages over the method disclosed by Aicher, including but not limited to the discovery of several crystalline intermediates which enabled increased quality control, reproducibility, and throughput. Not withstanding these advantages, several throughput limiting chromatographic purifications remained particularly relating to the C14-C26 fragment. For example, the C14-C26 fragment contains 4 chiral centers at C17, C20, C23, and C25 which require chromatography to control the quality of this fragment. More specifically, installment of the C25 chiral center does not occur with high selectivity and could not be practically enhanced due to a lack of crystalline intermediates late in the C14-C26 synthesis.

What is needed is a more efficient, less costly, more practical method for the synthesis of halichondrin B analogs, in particular B-1939.

SUMMARY

The current invention relates to a method for the synthesis of Halichondrin B analogs, such as B-1939, from (−)-quinic acid according to the process illustrated in Scheme 1, below. The method introduces a number of new and crystalline intermediates which greatly improve the stereochemical quality of the compounds synthesized and reduces the need for chromatographic steps. Unlike the previously described methods, the presently claimed method is substantially more appropriate for pharmaceutical manufacturing.

The invention also pertains to the novel intermediates disclosed herein.

Scheme 1

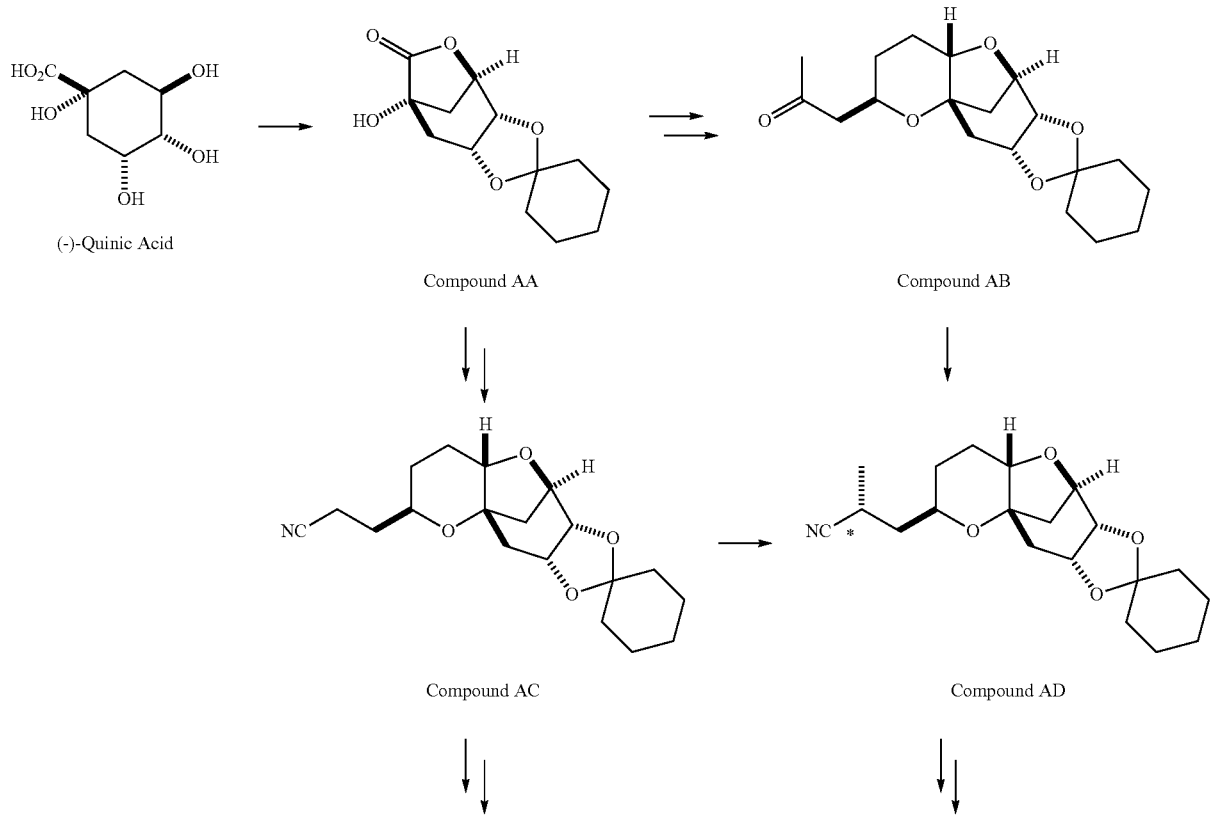

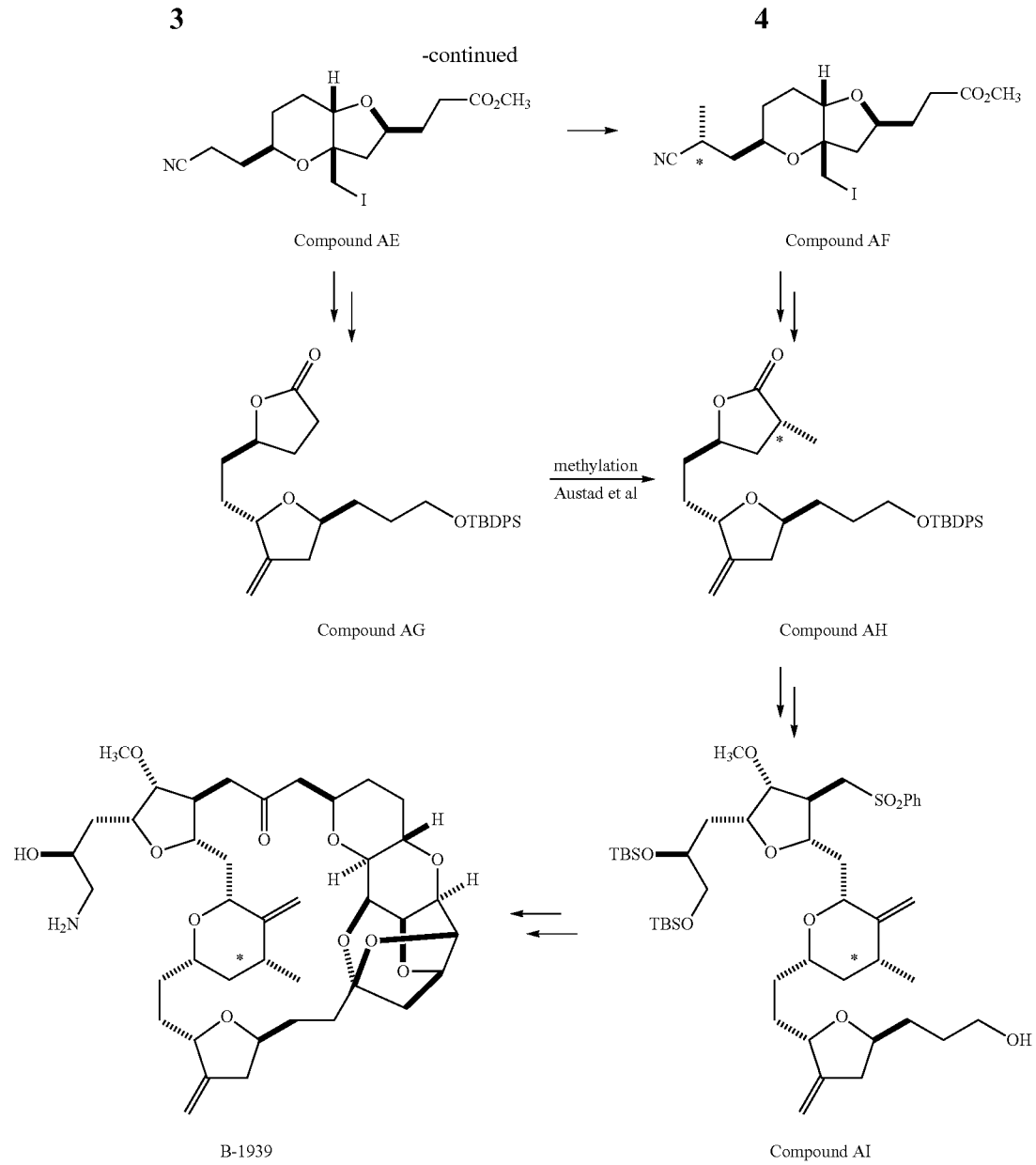

WO 2005/118565 disclosed a method for making Halichondrin B analogs, such as B-1939, that included synthetic routes for (1) producing the compound of formula Ia from (−)-quinic acid, and for (2) producing the B-1939 from Compound AG. Both synthetic routes are suitable for use in the method of the present invention, and are incorporated by reference herein.

The method of the present invention differs from the method disclosed in WO 2005/118565 in the process of synthesizing Compound AH from Compound AA. In particular, the present invention discloses highly efficient methods for generating the C25 chiral center, marked with an asterisk(*) in the relevant compounds in Scheme 1, by a process of equilibrating and selectively crystallizing the desired C25 isomer via an alpha-methylated nitrile. In the method described in WO 2005/118565, Compound AH is synthesized by adding a methyl group to Compound AG, as shown above. This reaction generates the C25 chiral center. The product of that reaction is a mixture of diastereomers with each possible configuration around that chiral center. Chromatography can be used to partially isolate Compound AH from the mixture of diastereomers, as disclosed in WO2005/118565; however, the remaining diastereomers of Compound AH result in undesired impurities in subsequent reaction steps, impurities which can only be removed through additional purification procedures.

Unlike the methods of syntheses of halichondrin B analogs previously described, the method of the present invention involves the formation of the C25 chiral center at an earlier stage in the synthesis of Compound AH. Several of the methylated intermediates, including Compound AD and Compound AF are crystallizable. By crystallizing one or more of the methylated intermediates in accordance with the methods of the present invention, one can produce a composition of comprising Compound AH that is substantially diastereomerically pure. For example, Compound AC can be methylated to produce Compound AD. When Compound AD is produced, a the C25 chiral center is produced, the same chiral center discussed with respect to Compound AH. When this reaction occurs, a diastereomeric mixture is produced with each possible stereomeric configuration around that chiral center. Although the methylation itself occurs with low stereoselectivity, surprisingly, the desired diastereomer of Compound AD stereoselectively crystallizes. Moreover, the undesired C25 stereoisomer can be epimerized under conditions from which the desired C25 stereoisomer crystallizes. Thus, the yield and quality of the C25 stereoisomer can be enhanced by crystallization induced dynamic resolution (CIDR).

Several other intermediates produced in the synthetic route from Compound AD to Compound AH can also be crystallized from reaction mixtures, resulting in an even higher purity composition of Compound AH than could be produced by previously disclosed methods. In particular, Compound AF is a crystalline compound, while the corresponding non-methylated Compound AE requires chromatography for purification. Compound AF may be synthesized from Compound AD or it can be synthesized by methylating Compound AE.

Removal of chromatography steps from the processes used to synthesize halichondrin B analogs dramatically increases the product yield and reproducibility, while decreasing cost and production time. The present method also enables one to resolve difficult to resolve chiral centers at a considerably earlier points in the process, even as early as the production of Compound AH and Compound AI. B-1939 is suitably synthesized from Compound AI using methods such as those described in WO/2005/118565.

In one embodiment, the invention pertains, at least in part, to a method of obtaining a substantially diastereomerically pure composition comprising a compound of formula (I). The method includes crystallizing the compound of formula (I) from a mixture of diastereomers under appropriate crystallization conditions, such that a substantially diastereomerically pure composition comprising a compound of formula (I) is formed. The compound of formula (I) is:

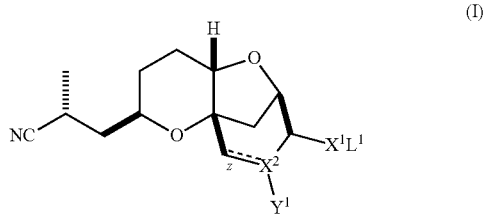

(I)

wherein:
z is a single or double bond, provided that when z is a double bond, $X^2$ is C and $Y^1$ is hydrogen; and provided that when z is single bond, $X^2$ is CH or O;

$X^1$ is O, S, or CN, provided that when $X^1$ is CN or S, $X^2$ is O;

$Y^1$ is a halide, hydrogen or O-$L^2$, or absent when $X^2$ is O; and $L^1$ and $L^2$ are independently selected from hydrogen and a protecting group, or $L^1$ and $L^2$ together are a protecting group, provided that when $X^1$ is CN, $L^1$ is absent; and salts thereof. The invention also pertains to compositions of compounds of formula (I) that are substantially free of diastereomers, as well as compounds of formula (I).

In another embodiment, the invention also pertains to a method of making a diastereomerically pure composition of a compound of formula (Ib) from a compound of formula (Ia), wherein the compound of formula (Ia) is:

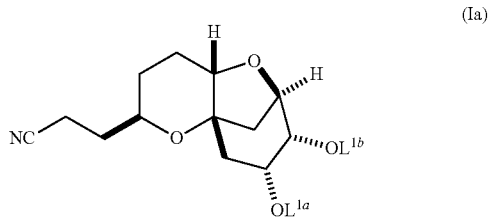

(Ia)

and the compound of formula (Ib) is:

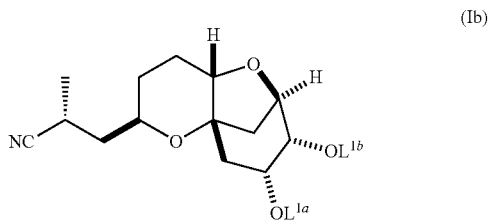

(Ib)

wherein $L^{1a}$ and $L^{1b}$ are independently selected from hydrogen and a protecting group, or $L^{1a}$ and $L^{1b}$ together are a divalent protecting group, provided that $L^{1a}$ of formulae (Ia) and (Ib) are the same and $L^{1b}$ of formulae (Ia) and (Ib) are the same. When $L^{1a}$ or $L^{1b}$ is a protecting group, it is preferably selected from the group consisting of $C_1$-$C_6$ alkyl ethers, aryl ($C_1$-$C_6$) alkyl ethers, silyl ($C_1$-$C_{10}$) ethers, $C_1$-$C_6$ alkyl esters, cyclic $C_1$-$C_6$ acetals, cyclic $C_2$-$C_7$ ketals, and cyclic carbonates. The method includes reacting the compound of formula (Ia) under alkylating conditions to form a mixture comprising the compound of formula (Ib) and diastereomers thereof; and crystallizing the compound of formula (Ib) from the mixture, under appropriate crystallization conditions.

In another embodiment, the invention pertains, at least in part, to a method of obtaining a substantially diastereomerically pure composition comprising a compound of formula (II). The method includes crystallizing the compound of formula (II) from a mixture of diastereomers under second appropriate crystallization conditions, such that a substantially diastereomerically pure composition comprising a compound of formula (II) is formed. The compound of formula (II) is:

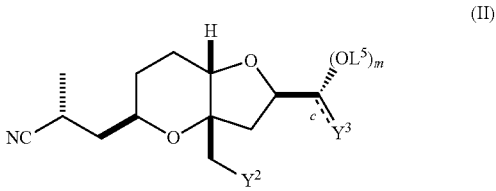

(II)

wherein:
c is a single or double bond, provided that when c is a double bond m is 0 and $Y^3$ is O or CHCO$_2$-$L^3$, and provided that when c is a single bond m is 0 or 1 and $Y^3$ is CH$_2$O-$L^3$, CH$_2$CO$_2$-$L^3$ or CH$_2$CH$_2$O-$L^3$;

$Y^2$ is $C_1$-$C_7$ sulfonate, O-$L^4$ or a halide;

$L^4$ is hydrogen or a protecting group; and $L^3$ and $L^5$ are each independently hydrogen or a protecting group, or $L^3$ and $L^5$ together are a protecting group, or a salt thereof. The invention also pertains to compositions of compounds of formula (II) that are substantially free of diastereomers, as well as compounds of formula (II).

In yet another embodiment, the invention also pertains to compounds of formula (III):

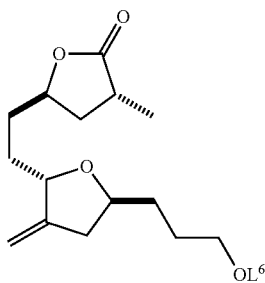

(III)

wherein: $L^6$ is hydrogen or a protecting group; and salts thereof.

In yet another embodiment, the invention also pertains to a composition comprising a compound of formula (IIIa):

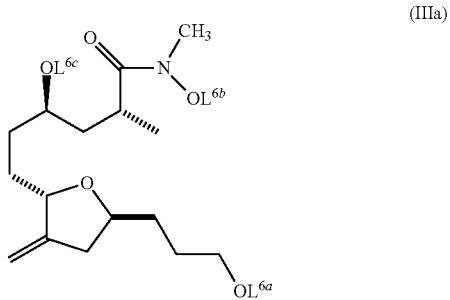

(IIIa)

$L^{6a}$, $L^{6b}$, and $L^{6c}$ are each protecting groups, or a salt thereof, and wherein the composition is substantially free of diastereomers.

Furthermore, the invention also pertains to a composition comprising a compound selected from the group consisting of formula (I), (Ia), (Ib), (Ic), (Id), (Ie), (II), (IIa), (IIb), (III) and (IIIa). The invention also pertains to each of the compounds described in herein.

DETAILED DESCRIPTION

The current invention pertains, at least in part, to methods and intermediates for the preparation and crystallization of intermediates and other compounds useful in the synthesis of halichondrin B and its analogs.

A. Definitions

In order that the present invention may be more readily understood, certain terms are first defined. Additional definitions are set forth throughout the detailed description.

The term "acetyl" refers to both acyl groups (e.g., —C(═O)—CH$_3$) and C$_1$-C$_8$ alkyl substituted carbonyls (e.g., —C—(═O)—(C$_1$-C$_7$)alkyl)). Preferably, the acetyl group is acyl.

The term "alkyl" refers to saturated hydrocarbons having one or more carbon atoms, including straight-chain alkyl groups (e.g., methyl, ethyl, propyl, butyl, pentyl, hexyl, etc.), cyclic alkyl groups (or "cycloalkyl" or "alicyclic" or "carbocyclic" groups) (e.g., cyclopropyl, cyclopentyl, cyclohexyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). The terms "alkenyl" and "alkynyl" refer to unsaturated aliphatic groups analogous to alkyls, but which contain at least one double or triple carbon-carbon bond respectively.

The term "alkoxy" refers to alkyl groups linked to the remainder of the molecule through an oxygen atom. Examples of alkoxy groups include, but are not limited to, methoxy, ethoxy, isopropyloxy, propoxy, butoxy, and pentoxy groups. The alkoxy groups can be straight-chain or branched. Preferable alkoxy groups include methoxy.

The term "heterocyclic group" refers to closed ring structures analogous to carbocyclic groups in which one or more of the carbon atoms in the ring is an element other than carbon, for example, nitrogen, sulfur, or oxygen. Heterocyclic groups may be saturated or unsaturated. Additionally, heterocyclic groups (such as pyrrolyl, pyridyl, isoquinolyl, quinolyl, purinyl, and furyl) may have aromatic character, in which case they may be referred to as "heteroaryl" or "heteroaromatic" groups. Exemplary heterocyclic groups include, but are not limited to pyrrole, furan, thiophene, thiazole, isothiazole, imidazole, triazole, tetrazole, pyrazole, oxazole, isooxazole, pyridine, pyrazine, pyridazine, pyrimidine, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine.

The term "amine" or "amino," refers to unsubstituted or substituted moiety of the formula —NR$^a$R$^b$, in which R$^a$ and R$^b$ are each independently hydrogen, alkyl, aryl, or heterocyclyl, or R$^a$ and R$^b$, taken together with the nitrogen atom to which they are attached, form a cyclic moiety having from 3 to 8 atoms in the ring. Thus, the term amino includes cyclic amino moieties such as piperidinyl or pyrrolidinyl groups, unless otherwise stated.

Regarding connectivity, an "arylalkyl" group, for example, is an alkyl group substituted with an aryl group (e.g., phenylmethyl (i.e., benzyl)). An "alkylaryl" moiety is an aryl group substituted with an alkyl group (e.g., p-methylphenyl (i.e., p-tolyl)). Thus, the term imidazolyl-alkyl refers to an alkyl group substituted with an imidazolyl moiety.

The term "sulfonate" refers to moieties of the formula: R—SO$_2$—O—, wherein R is C$_1$-C$_4$ alkyl or C$_6$-C$_8$ aryl. Examples of sulfonates include, methanesulfonate (mesylate), trifluoromethanesulfonate (triflate), p-toluenesulfonate (tosylate), and benzenesulfonate (bensylate).

As used in the description and drawings, an optional single/double bond is represented by a solid lines together with a second dashed line, and refers to a covalent linkage between two carbon atoms which can be either a single bond or a double bond. For example, the structure:

can represent either butane or butene.

The term "protecting group" refers to moieties which may be cleaved from the compound to yield a hydroxy group, a thiol group, a carboxylic acid group, or another functional group which a person of skill in the art desires to protect.

Generally, protecting groups are selected such that they resist cleavage during reactions focused on other portions of the molecule. Protecting groups can be selected such that they are acid labile (e.g., cleavable in the presence of acid), base labile (e.g., cleavable in the presence of base), or otherwise selectively cleavable. Protecting groups are well known to those of skill in the art. Examples of suitable protecting groups can be found, for examples in "Protective Groups in Organic Synthesis," 3$^{rd}$ edition, John Wiley & Sons, Inc.

Examples of protecting groups, include, but are not limited to $C_1$-$C_{12}$ alkylcarbonyls, $C_1$-$C_6$ alkyls, $C_1$-$C_{15}$ alkyl silyl moieties (e.g., moieties which form alkyl silyl ethers when bonded to an adjacent oxygen), aryl($C_1$-$C_6$) alkyls, carbonates, and $C_1$-$C_6$ alkoxy-($C_1$-$C_6$)alkyls (e.g., methoxymethyl).

Examples of $C_1$-$C_{10}$ alkyl silyl protecting groups include, but are not limited to, trimethylsilyl, triethylsilyl, t-butyldimethylsilyl, t-butyldiphenylsilyl, or triisopropylsilyl (e.g., trimethylsilyl ether, triethylsilyl ether, t-butyldimethylsilyl ether, t-butyldiphenylsilyl ether, or triisopropylsilyl ether when taken together with an adjacent oxygen). Preferably, the alkyl silyl protecting group is t-butyldimethylsilyl ether.

Examples of $C_1$-$C_6$ alkyl protecting groups include methyl and t-butyl (e.g., methyl ethers and t-butyl ethers when taken together with an adjacent oxygen).

Examples of aryl ($C_1$-$C_6$) alkyl protecting groups include is 3,4-dimethoxybenzyl, p-methoxybenzyl, benzyl, or trityl (e.g., 3,4-dimethoxybenzyl ether, p-methoxybenzyl ether, benzyl ether or trityl ether when taken together with an adjacent oxygen).

Compounds with two or more groups to be protected (e.g., hydroxy and/or thiol groups) may be protected together using a protecting group which attaches to both of the hydroxy and/or thiol groups for which protection is desired. These protecting groups are also referred to herein as "divalent protecting groups." Examples of divalent protecting groups which protect two hydroxy and/or thiol groups include, but are not limited to $C_1$-$C_6$ acetals, $C_2$-$C_6$ ketals, and cyclic carbonates. Examples of cyclic protecting groups include, but are not limited to, acetonide, benzylidine, and, preferably, cyclohexylidine. Examples of protecting groups which protect two hydroxy and or thiol groups include those shown below. The arrows designate where the moiety is attached to the hydroxy or thiol groups on the compound:

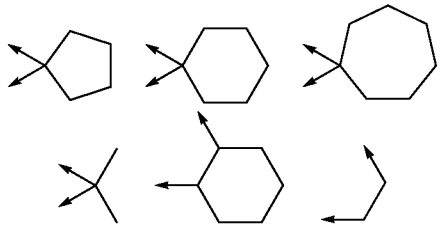

The term "acceptable salts" refers to salts of the compounds of the invention which are acceptable for the methods of the invention, e.g., the synthesis of intermediates of halichondrin B analogs.

The compounds of the invention that are acidic in nature are capable of forming a wide variety of base salts. The chemical bases that may be used as reagents to prepare acceptable base salts of those compounds of the invention that are acidic in nature are those that form base salts with such compounds. Such base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The base addition salts of compounds of the invention that are acidic in nature may be formed with cations by conventional methods.

The term "anti-solvent" includes organic solvents in which the compound of interest is not substantially soluble in. Examples of anti-solvents for the compounds of the present invention of formula (II) include non-polar organic solvents, such as heptane.

The term "alkylating reagent" refers to a reagent which is capable of adding an alkyl group, preferably a methyl group, to particular organic compounds described herein including, but not limited to, compounds of formula (Ia). Preferably, the alkylating reagent is a $C_1$-$C_4$ alkyl halide (preferably MeI) or a sulfonate.

The term "appropriate alkylating condition" refers to conditions which are selected such that an alkylating reaction is able to be performed. These conditions include an aprotic solvent (e.g., tetrahydrofuran, toluene, or t-butyl methyl ether) and a base (e.g., a metal amide or a metal alkoxide). Examples of bases which may be used in the alkylating conditions include, but are not limited to, LDA, KHMDS, and potassium t-butoxide.

The language "appropriate crystallization conditions" refers to conditions which are selected such that the desired diastereomer of a particular compound is crystallized, preferably a compound of formula (I) or (Ib). Examples of solvent systems that may be used to perform this crystallization include, but are not limited to, heptane and mixtures of heptane with one or more co-solvents, such as, but not limited to tert-butyl methyl ether and isopropanol. The ratio of heptane to tert-butyl methyl ether or isopropanol is selected such that the desired diastereomer is crystallized. The ratio may range from about 5:1 to about 3:1, and is preferably about 4:1. The appropriate conditions may also include the addition of a base. Examples of such bases include $C_1$-$C_6$ alkoxides (e.g., t-butyl oxide or isopropoxide). Alternatively, other solvent systems may also be used, such as, combinations of a protic solvent and an anti-solvent.

The language "second appropriate crystallization conditions" refers to conditions which are selected such that the desired diastereomer of a particular compound is crystallized, preferably a compound of formula (II) or (IIa). Examples of second appropriate crystallization conditions for the crystallization of compounds of formula (II) and/or (IIa) include dissolving the compound in a polar solvent (e.g., MTBE) and optionally adding an anti-solvent to precipitate the compound.

The term "contacting" refers to any interaction between two or more compounds which results in a chemical reaction, such as, but not limited to, the creation or the cleavage of one or more chemical bonds.

The language "mixture of diastereomers" refers to compositions which comprise two or more diastereomers.

The term "protic solvent" refers to a solvent which contains a dissociable H$^+$ or a group capable of forming hydrogen bonds (e.g., hydroxyl or amine group). Examples are water, methanol, ethanol, formic acid, hydrogen fluoride and ammonia. Preferred protic solvents include alcohols, such as isopropanol.

The language "substantially diastereomerically pure composition" refers to compositions which the ratio of a particular compound to the compound with the opposite stereochemistry at the chiral center indicated with an asterisk in Scheme 1 is at least about 8:1 or greater, at least about 10:1 or greater, at least about 15:1 or greater, at least about 20:1 or greater, or, preferably, at least about 30:1 or greater. Diastereomeric purity can be enhanced using multiple kinetic or crystallization induced dynamic resolutions. It also can be enhanced by repeated recrystallizations.

The language "substantially no chromatography" refers to methods of synthesis which use 4 or fewer, 3 of fewer, 2 or fewer, 1 or fewer, or no chromatography steps. Preferably, the term refers to methods of synthesis which do not require preparative HPLC steps.

Certain abbreviations and acronyms are used herein. Definitions for these abbreviations and acronyms are listed below:
ACN Acetonitrile
AcOH Acetic Acid
CIDR Crystallization induced dynamic resolution
DBU Diazabicycloundecane
DCM Dichloromethane
DIBAL Diisobutylaluminium hydride
DME Dimethoxyethane
DMF Dimethylformamide
ESI Electron spin injection
$Et_3N$ Triethylamine
EtOAc Ethyl acetate
EtOH Ethanol
FDA Food and Drug Administration
HPLC High pressure liquid chromatography
IPA Isopropanol
$^iPr_2NEt$ Diisopropylethylamine
KHMDS Potassium-Hexamethyldisilazane
$KO^tBu$ Potassium tert-butoxide
LDA Lithium diisopropyl amide
LRMS Low resolution mass spectrometry
MeI Methyl iodide
MeOH Methanol
MsCl Mesyl chloride (methanesulfonyl chloride; $CH_3SO_2Cl$)
MTBE Methyl tert-butyl ether
MsO— Mesylate (methanesulfonate)
NaOEt Sodium ethoxide
NaOMe Sodium methoxide
NBS N-bromosuccinimide
NIS N-iodosuccinimide
NMR Nuclear magnetic resonance
$Ph_3P$ Triphenyl phosphine
TBDPSCl tert-Butyl diphenyl silyl chloride
TBME tert-Butyl methyl ether
TBS tert-Butyldimethyl silyl
TBSCl tert-Butyldimethyl silyl chloride
TBSOTf tert-Butyldimethylsilyl trifluoromethanesulphonate
$^tBuOK$ Potassium tert-butoxide
TEA Triethylamine
TESOTf Triethylsilyl trifluoromethanesulfonate
TsCl Tosyl chloride (p-toluenesulfonyl chloride)
TfO— Triflate (trifluoromethanesulfonate)
$Tf_2O$ Triflic anhydride $(CF_3SO_2)_2O$
TsO— Tosylate (p-toluenesulfonate)
THF Tetrahydrofuran
TsOH p-Toluene sulfonic acid
TosMIC Toluenesulfonylmethyl isocyanide
Trt Trityl (Triphenylmethyl)

B. Compounds

In one embodiment, the invention pertains to a compound of formula (I):

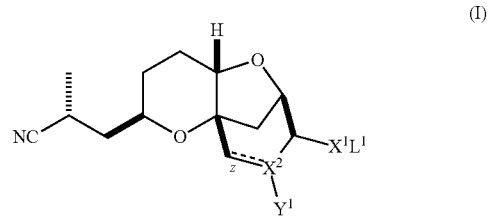

wherein:
z is a single or double bond, provided that when z is a double bond, $X^2$ is C and $Y^1$ is hydrogen; and provided that when z is single bond, $X^2$ is CH or O;

$X^1$ is O, S, or CN, provided that when $X^1$ is CN or S, $X^2$ is O;

$Y^1$ is a halide, hydrogen or O-$L^2$, or absent when $X^2$ is O; and $L^1$ and $L^2$ are independently selected from hydrogen and a protecting group, or $L^1$ and $L^2$ together are a protecting group, provided that when $X^1$ is CN, $L^1$ is absent; and salts thereof. The invention also pertains to compounds of formula (I).

In an embodiment, $L^1$ and/or $L^2$ are each independently a silyl ether, a $C_1$-$C_8$ alkyl ether, an acyl (—C(=O)$CH_3$), or acetyl group. Preferably, $X^1$ is oxygen.

Preferably, $L^1$ and $L^2$ may represent the same protecting group attached to the molecule through both the O of $X^2$ when $Y^1$ is O-$L^2$ and $X^1$. Examples of such protecting groups include, but are not limited to, cyclic $C_1$-$C_6$ acetals, cyclic $C_2$-$C_6$ ketals, and cyclic carbonates. In a further embodiment, $L^1$ and $L^2$ are linked to a single divalent protecting group. Examples of divalent protecting groups include acetonides, benzylidines, and preferably, cyclohexylidine. In certain embodiments, when both $L^1$ and $L^2$ are protecting groups, $L^1$ and $L^2$ when taken together may form a pentane, hexane, or pyran ring and link to $X^1$ to $X^2$ through a single carbon atom. Preferably, when $Y^1$ is O-$L^2$; $X^1$ is O or S; $L^1$ and $L^2$ together form protecting group which is a $C_4$-$C_7$ alkyl ring with one member of the ring covalently linked to the O of O-$L^2$ and to $X^1$.

In one embodiment, $X^2$ is CH, $Y^1$ is O-$L^2$, and $X^1$ is O.

In another embodiment, when $Y^1$ is a halide, it is fluoride, chloride, iodide, or, preferably, bromide. In another further embodiment, $L^1$ is acetyl.

In another embodiment, when z is a double bond, Y is hydrogen, and $X^2$ is C. In another further embodiment, $X^1$ is oxygen and $L^1$ is a protecting group (when taken together with $X^1$) selected from the group consisting of $C_1$-$C_6$ alkyl ether, aryl ($C_1$-$C_6$) alkyl ether, $C_1$-$C_6$ ester, and a silyl ($C_1$-$C_{10}$) ether.

In another further embodiment, $X^2$ is oxygen, when z is a single bond. In another further embodiment, $L^1$ is hydrogen. In another further embodiment, $L^1$ is a protecting group selected from a glycoside, $C_1$-$C_6$ alkyl, $C_1$-$C_6$ acetyl, and a $C_1$-$C_6$ ester.

Preferably, the compound of formula (I) is a compound of formula (Ib):

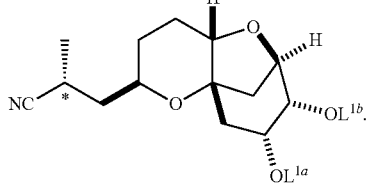

(Ib)

wherein $L^{1a}$ and $L^{1b}$ are hydrogen, independently selected protecting groups, or together a single divalent protecting group.

In a further embodiment, $L^{1a}$ and $L^{1b}$ are each protecting groups selected from $C_1$-$C_6$ alkyl ethers, aryl ($C_1$-$C_6$) alkyl ethers, silyl ($C_1$-$C_{10}$) ethers, $C_1$-$C_6$ alkyl esters, cyclic $C_1$-$C_6$ acetals, cyclic $C_2$-$C_7$ ketals, and cyclic carbonates.

In a further embodiment, the invention pertains to a composition comprising a compound of formula (Ib), wherein the composition is substantially diastereomerically pure. In a further embodiment, the ratio of compounds of formula (Ib) to the compounds with the opposite stereochemistry at the chiral center marked with the asterisk is at least about 8:1 or greater, at least about 20:1 or greater, or, preferably, at least about 30:1 or greater.

In a further embodiment, the compound of formula (I) is selected from the group consisting of:

Compound AD

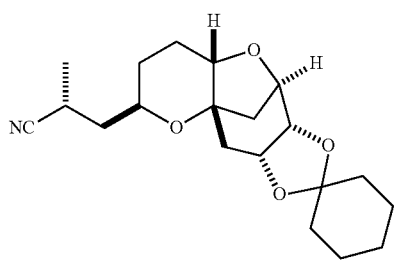

Compound AJ

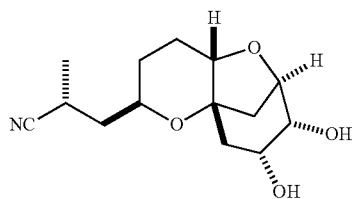

Compound AK

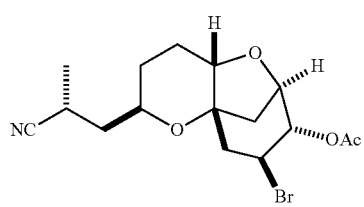

Compound AL

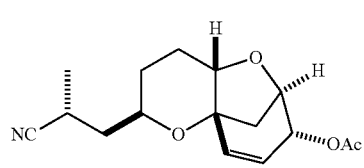

Compound AM

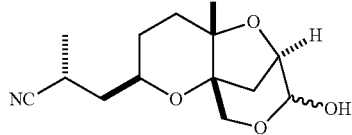

or a salt thereof.

In another embodiment, the invention pertains to a compound of formula (II):

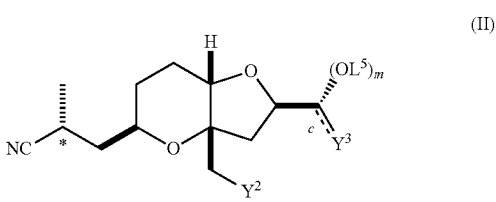

(II)

wherein:
c is a single or double bond, provided that when c is a double bond m is 0 and $Y^3$ is O or $CHCO_2$-$L^3$, and provided that when c is a single bond m is 0 or 1 $Y^3$ is $CH_2O$-$L^3$, $CH_2CO_2$-$L^3$ or $CH_2CH_2O$-$L^3$;
$Y^2$ is $C_1$-$C_7$ sulfonate, O-$L^4$ or a halide;
$L^4$ is hydrogen or a protecting group; and
$L^3$ and $L^5$ are each independently hydrogen or a protecting group, or $L^3$ and $L^5$ together are a protecting group, or a salt thereof.

Examples of $Y^2$ include halides, e.g., fluoride, chloride, bromide, or preferably, iodide. In another embodiment, $Y^2$ is O-$L^4$. Examples of $L^4$ include hydrogen. In another embodiment, c is a double bond. Examples of $Y^3$ when c is a double bond include $CHCO_2$-$L^3$. Examples of $L^3$ groups include $C_1$-$C_6$ alkyl, e.g., methyl.

In another embodiment, c is a single bond. Examples of $Y^3$ when c is a single bond include $CH_2CH_2$—$OL^3$. In a further embodiment, $L^3$ and $L^5$ may be linked to form a cyclic $C_1$-$C_6$ acetal or a cyclic $C_2$-$C_7$ ketal.

In a further embodiment, $Y^3$ is $CH_2CO_2$-$L^3$ and $L^3$ is $C_1$-$C_{10}$ alkyl, $C_4$-$C_{10}$ aryl-$C_1$-$C_6$ alkyl, or $C_4$-$C_{10}$ aryl. In another further embodiment, $Y^2$ is a halide, e.g., iodide.

In a further embodiment, the invention pertains to a composition comprising a compound of formula (II), wherein the composition is substantially diastereomerically pure. In a further embodiment, the ratio of compounds of formula (II) to the compounds with the opposite stereochemistry at the chiral center marked with the asterisk is at least about 8:1 or greater, at least about 20:1 or greater, or, preferably, at least about 30:1 or greater.

In another further embodiment, the compound of formula (II) is selected from the group consisting of:

Compound AN

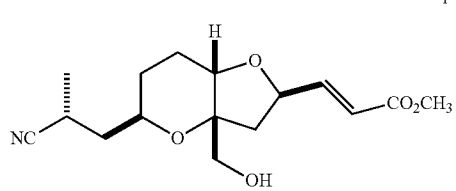

Compound AO

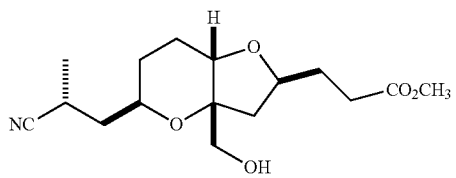

Compound AF

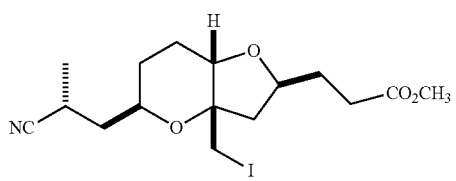

Compound AP

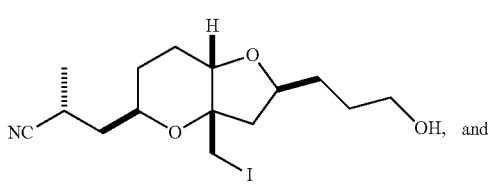

Compound AQ

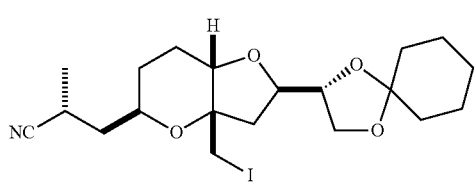

or a salt thereof.

The invention also pertains to compositions comprising the compounds shown above substantially free of diastereomers.

In a further embodiment, the invention also pertains to a compound of formula (IIa):

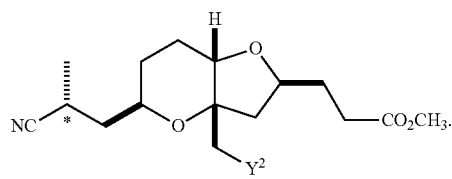

(IIa)

In a further embodiment, the compound of formula (IIa) is substantially free of diastereomers, e.g., a compound with the opposite stereochemistry at the chiral carbon indicated with an asterisk in the formula above. In an embodiment, the invention pertains to a substantially diastereomerically pure composition comprising a compound of formula (IIa), wherein the ratio of compounds of formula (IIa) to compounds with the opposite stereochemistry at the chiral center marked with the asterisk is at least about 8:1 or greater, at least about 20:1 or greater, or, preferably, at least about 30:1 or greater.

The compound of formula (IIa) is particularly important because while it is crystalline, the corresponding non-methylated intermediate is not crystalline and requires purification via chromatography. The invention also pertains to a compounds of formula (IIa) in crystalline form.

In another embodiment, the invention pertains to a compound of formula (III):

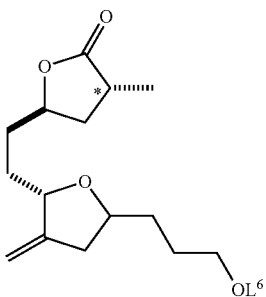

(III)

wherein: $L^6$ is hydrogen or a protecting group; or an acceptable salt thereof. In an embodiment, the invention pertains to a substantially diastereomerically pure composition comprising a compound of formula (III), wherein the ratio of compounds of formula (III) to compounds with the opposite stereochemistry at the chiral center marked with the asterisk is at least about 8:1 or greater, at least about 20:1 or greater, or, preferably, at least about 30:1 or greater.

In a further embodiment $L^6$ is hydrogen or, when taken together with the oxygen to which it is bound, a silyl $C_1$-$C_{10}$ ether. Examples of such silyl $C_1$-$C_{10}$ ethers include, but are not limited to, trimethylsilyl ether, triethylsilyl ether, t-butyldimethylsilyl ether, t-butyldiphenylsilyl ether, or triisopropylsilyl ether.

In a further embodiment, the compound of formula (III) is:

Compound AR

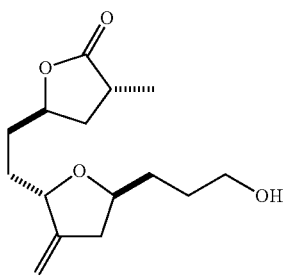

Compound AH

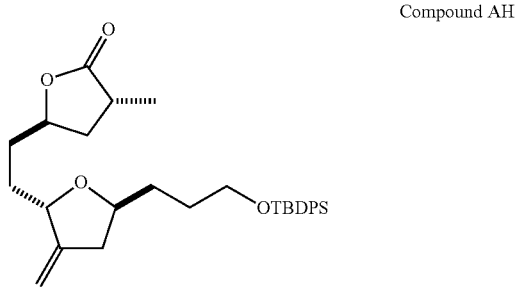

The invention also pertains to compositions comprising the compounds shown above substantially free of diastereomers.

In another embodiment, the invention pertains to compounds of formula (IIIa):

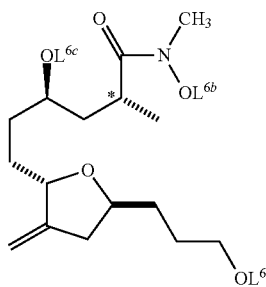

wherein $L^{6a}$, $L^{6b}$, and $L^{6c}$ are each protecting groups, or a salt thereof. In a further embodiment, the invention pertains to a composition comprising the compound of formula (IIIa) wherein the composition is substantially free of diastereomers (e.g., compounds with the opposite stereochemistry at the chiral center indicated with an asterisk in formula (IIIa) above).

The invention also pertains, at least in part, to compounds of formula (Id):

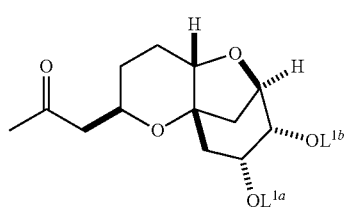

wherein $L^{1a}$ and $L^{1b}$ are independently selected from hydrogen and a protecting group, or $L^{1a}$ and $L^{1b}$ together are a divalent protecting group, or a salt thereof.

C. Methods

In one embodiment, the invention pertains to a method of obtaining a substantially diastereomerically pure composition comprising a compound of formula (I). The method includes crystallizing the compound of formula (I) from a mixture of diastereomers under appropriate crystallization conditions, such that a substantially diastereomerically pure composition comprising a compound of formula (I) is formed.

The mixture of diastereomers is preferably a mixture of compounds of formula (I) with compounds of formula (Ie), wherein said compounds of formula (Ie) is:

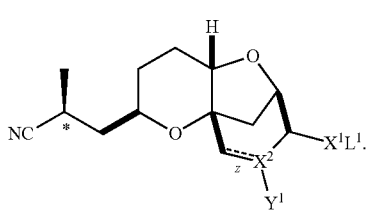

In one embodiment, the substantially diastereomerically pure composition comprises a ratio of compounds of formula (I) to compounds of formula (Ie) of at least about 8:1 or greater, of at least about 10:1 or greater, of at least about 20:1 or greater, or, preferably, at least about 30:1 or greater. In order to increase the diastereomeric purity of the compound of formula (I), additional recrystallizations of the compound under similar appropriate conditions may be conducted.

The appropriate crystallization conditions are selected such that the desired diastereomer is crystallized. Examples of solvent systems that may be used to perform this crystallization include, but are not limited to, heptane/tert-butyl methyl ether and heptane/isopropanol. The appropriate conditions may also include the addition of a base. Examples of such bases include $C_1$-$C_6$ alkoxides (e.g., t-butyl oxide or isopropoxide).

Alternatively, other solvent systems may also be used, such as, combinations of a protic solvent (e.g., an alcohol, e.g., isopropanol) and an anti-solvent (e.g., non-polar organic solvent, e.g., heptane).

In a further embodiment, the invention also pertains to a method of synthesizing the compound of formula (Ib) from a compound of formula (Ia) by contacting a compound of formula (Ia) with an alkylating reagent under appropriate alkylating conditions. The compound of formula (Ia) is:

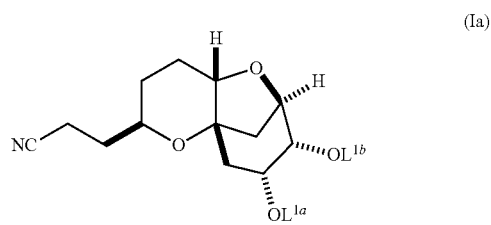

and the compound of formula (Ib) is:

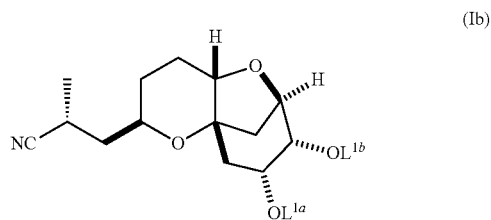

wherein $L^{1a}$ and $L^{1b}$ are independently selected from hydrogen and a protecting group, or $L^{1a}$ and $L^{1b}$ together are a divalent protecting group, provided that $L^{1a}$ of formulae (Ia) and (Ib) are the same and $L^{1b}$ of formulae (Ia) and (Ib) are the same. The method includes reacting the compound of formula (Ia) under alkylating conditions to form a mixture comprising the compound of formula (Ib) and diastereomers thereof; and crystallizing the compound of formula (Ib) from the mixture, under appropriate crystallization conditions.

In order to increase the diastereomeric purity of the compound of formula (Ib), additional recrystallizations of the compound under similar appropriate conditions may be conducted. Preferably, the mixture of diastereomers after two or more crystallizations results in a ratio of compounds of formula (Ib) to compounds with the opposite stereochemistry around the chiral center indicated with the asterisk above in formula (Ib) to be at least about 8:1 or greater, at least about 10:1 or greater, at least about 20:1 or greater, or at least about 30:1 or greater.

In yet another embodiment, the invention also pertains, at least in part, to a method of obtaining a substantially diastereomerically pure composition comprising a compound of formula (I). The method includes contacting a mixture of diastereomers with a base at an appropriate temperature, such that a substantially diastereomerically pure composition comprising a compound of formula (I) is formed.

Examples of bases which may be used in the method include bases known in the art, such as amide bases, metal alkoxides and KHMDS. The base may be present in any amount such that the desired diastereomer is formed. Preferably, the base is present in sub stoichiometric amounts (e.g., less than one equivalent). In another further embodiment, the appropriate temperature is less than about −30° C. In a further embodiment, the compound of formula (I) is a compound of formula (Ib).

If kinetic resolution of the stereocenter is desired, the compound of formula (I) or (II) may be treated with substoichiometric amounts of a strong base (e.g., an amide base, e.g., KHMDS) at low temperatures (e.g., less than about −30° C.). Once the reaction has taken place, compounds of formula (I) or (II) may be isolated from an appropriate crystallization solvent system and recrystallized. Examples of solvent systems which may be used include, but are not limited to, heptane, heptane/t-butyl methyl ether and heptane/isopropanol.

Alternatively, crystallization induced dynamic resolution (CIDR) may also be used to enhance the diastereomeric purity of compounds of formula (I) and/or (II). For example, compounds of formula (I) and/or (II) may be treated with a weak base, such as an alkoxide, (e.g., potassium t-butyl oxide or potassium isopropoxide) in an appropriate crystallization solvent system. Examples of appropriate crystallization solvent systems include combinations of a protic solvent (e.g., isopropanol) and an anti-solvent (e.g., heptane) at non-cryogenic temperatures to provide purified compounds of formula (I) or (II).

In another embodiment, the invention pertains to a method of obtaining a substantially diastereomerically pure composition comprising a compound of formula (II). The method includes crystallizing the compound of formula (II) from a mixture of diastereomers under appropriate crystallization conditions, such that a substantially diastereomerically pure composition comprising a compound of formula (II) is formed.

In one embodiment, the composition comprises a ratio of compounds of formula (II) to compounds of formula (IIb) of at least about 8:1 or greater, at least about 10:1 or greater, at least about 20:1 or greater, or, preferably, at least about 30:1 or greater. The compound of formula (IIb) is:

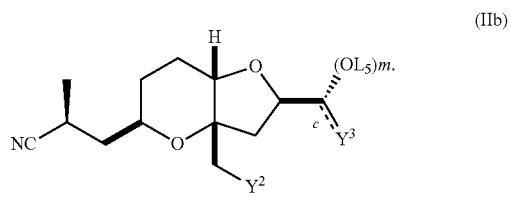

In order to increase the diastereomeric purity of the compound of formula (II), additional recrystallizations of the compound under similar appropriate conditions may be conducted.

In another embodiment, the invention also pertains to a method of synthesizing a compound of formula (IIa) from a compound of formula (Ib). The method includes selectively crystallizing a compound of formula (Ib) under appropriate crystallization conditions; and reacting the compound of formula (Ib), under appropriate conditions, such that a compound of formula (IIa) is formed. Preferably, the compound of formula (IIa) is formed using substantially no chromatography. The compound of formula (Ib) may be reacted under appropriate conditions to form a compound of formula (IIa), after having had been diastereomerically purified using recrystallization. Furthermore, the appropriate conditions may comprise dissolving a crystallized compound of formula (Ib) in a solvent before reacting it under appropriate conditions to form a compound of formula (IIa).

Appropriate conditions for the synthesis of compounds of formula (IIa) from compounds of formula (Ib) are described, for example, in Schemes 5, 6, 8, 9, and 10. Methods for selectively crystallizing a compound of formula (I) or (Ib) from a mixture of diastereomers under appropriate crystallization conditions has been described above.

The invention also pertains, at least in part, to a method of synthesizing a compound of formula (IIIa) from a compound of formula (IIa). The method includes crystallizing a compound of formula (IIa) under second appropriate crystallization conditions; reacting the compound of formula (IIa) under appropriate conditions such that a compound of formula (IIIa) is formed.

Examples of second appropriate crystallization conditions for the crystallization of compounds of formula (IIa) include dissolving the compound in a polar solvent (e.g., MTBE) and optionally adding an anti-solvent to precipitate the compound. Examples of anti-solvents which may be used include heptane. Preferably, the compound of formula (IIa) is reacted under appropriate conditions to form a compound of formula (IIIa), after having had been crystallized.

In another embodiment, the invention also pertains to a method of synthesizing a compound of formula (IIIa) from a compound of formula (Ib). The method includes selectively crystallizing a compound of formula (Ib) under appropriate crystallization conditions; and reacting the compound of formula (Ib) under appropriate conditions such that a compound of formula (IIIa) is formed. Preferably, the compound of formula (IIIa) is formed using substantially no chromatography.

The compound of formula (Ib) may be reacted under appropriate conditions to form a compound of formula (IIIa), after having had been diastereomerically purified using recrystallization. Furthermore, the appropriate conditions may comprise dissolving a crystallized compound of formula (Ib) in a solvent before reacting it under appropriate conditions to form a compound of formula (IIIa).

In another embodiment, the invention pertains to a method of synthesizing compounds of formula (IV). The method includes crystallizing a compound of formula (Ib) from a mixture of diastereomers under appropriate crystallization conditions, as described above; reacting the selectively crystallized compound of formula (Ib) with appropriate reagents, such that a compound of formula (IV) is synthesized. The compound of formula (IV) is:

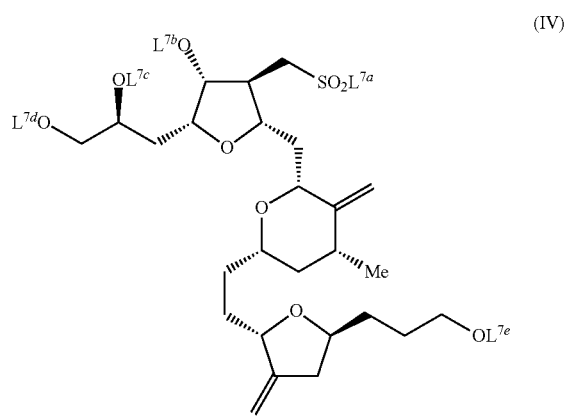

(IV)

wherein each of $L^{7a}$, $L^{7b}$, $L^{7c}$, $L^{7d}$, and $L^{7e}$ are each a protecting group or hydrogen. Examples of $L^{7a}$ include phenyl. Examples of $L^{7b}$ include methyl. Examples of $L^{7c}$ and $L^{7d}$ include TBS. Examples of $L^{7e}$ includes hydrogen.

Examples of appropriate reagents which may be used to synthesize compounds of formula (IV) from a compound of formula (Ib) include those described in Schemes 5, 6, 8, and 9 to form a compound of formula (IIIa). Methods which may be used to convert a compound of formula (IIIa) to a compound of formula (IV) are described in greater detail in WO/2005/118565, incorporated herein by reference in its entirety.

The compound of formula (Ib) may be reacted under appropriate conditions to form a compound of formula (IV), after having had been diastereomerically purified using recrystallization. Furthermore, the appropriate conditions may comprise dissolving a crystallized compound of formula (Ib) in a solvent before reacting it under appropriate conditions to form a compound of formula (IV).

In a further embodiment, the compound of formula (IV) is formed in greater than about 50% yield, greater than about 60% yield, or greater than about 70% yield from a compound of formula (Ib).

In a further embodiment, the invention also pertains to compounds of formula (I), (Ia), (Ib), (Ic), (Id), (Ie), (II), (IIa), (IIb), (III), (IIIa), (IV), (V), or otherwise described herein. The invention also pertains to compositions comprising compounds of any one of these formulae, substantially free of diastereomers. The invention also pertains to each of the intermediates and processes described herein.

In a further embodiment, the invention pertains to compositions comprising the compounds described herein substantially free of diastereomers, e.g., compounds with the opposite stereochemistry at the chiral carbon indicated with the asterisk in Scheme 1. The invention also pertains to methods of using these compounds to synthesize compounds of formula (IV), B-1939, or other halichondrin B analogs.

Te invention pertains, at least in part, to methods and intermediates for the conversion of compounds of formula (I) to compounds of formula (III). Compounds of formula (III) may further be converted to compounds of formula (IV) and/or halichondrin B or analogs thereof.

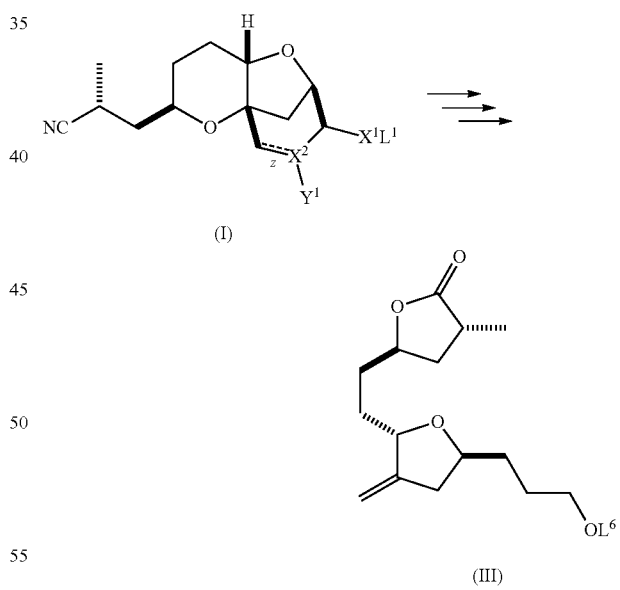

The compounds of formula (III) can be synthesized by methods described herein. The invention pertains, at least in part, to all compounds and intermediates described herein and the processes of synthesizing the compounds and intermediates.

Conversion of Compound 2-1 to a Compound of Formula (Ib)

Compounds of formula (Ib) can be synthesized from compounds of formula 2-1, as shown in Scheme 2:

Scheme 2

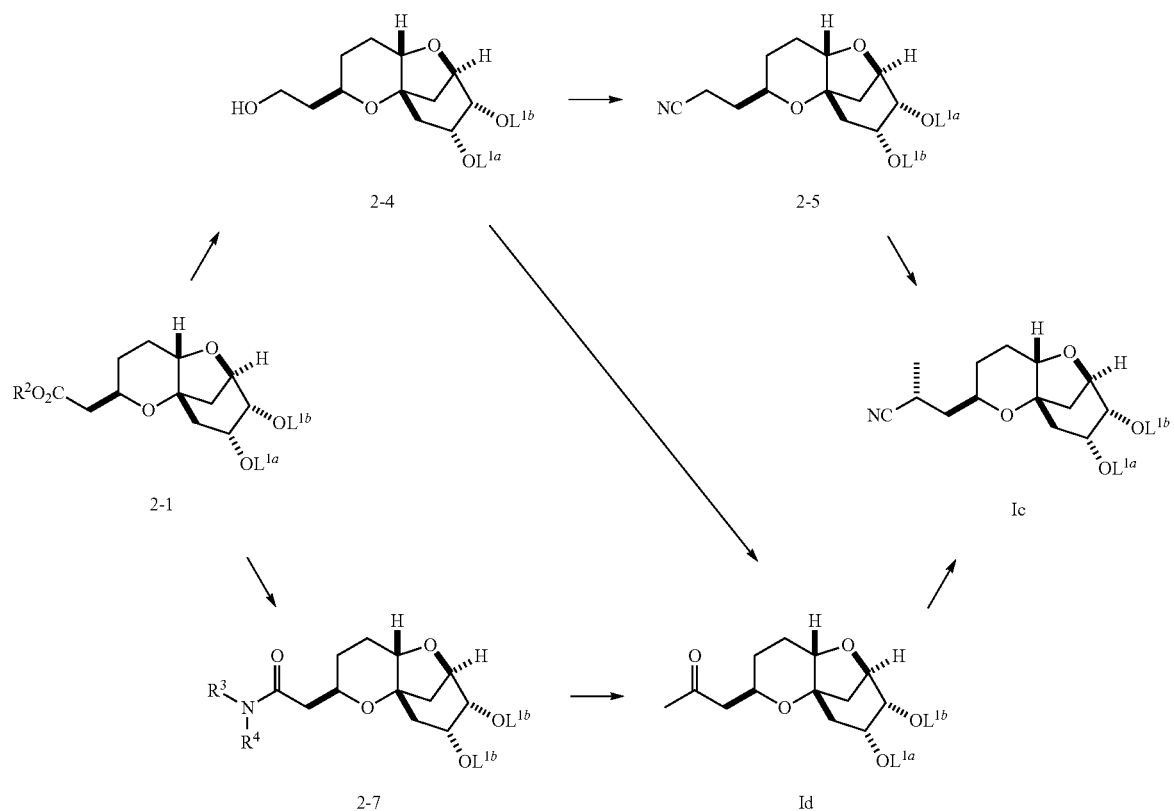

Compound 2-1 may be converted to compound (Ib). In Scheme 2, $L^{1a}$ and $L^{1b}$ are protecting groups. Examples of protecting groups include, but are not limited to $C_1$-$C_6$ alkyl ethers, aryl ($C_1$-$C_6$) alkyl ethers, silyl ($C_1$-$C_{10}$) ethers, $C_1$-$C_6$ alkyl esters, cyclic $C_1$-$C_6$ acetals, cyclic $C_2$-$C_7$ ketals, and cyclic carbonates. Examples of $R^2$ include hydrogen, $C_1$-$C_6$ alkyl (e.g., methyl, t-butyl, etc.), $C_4$-$C_{10}$ aryl (e.g., phenyl), and $C_4$-$C_{10}$ aryl-$C_1$-$C_6$ alkyl groups (e.g., benzyl). Examples of $R^3$ and $R^4$ include $CH_3$ and $OCH_3$ respectively, or $R^3$ and $R^4$ taken together can be (—$CH_2CH_2$)$_2$O.

Compound 2-1 can be converted to compound 2-4 through the use of an appropriate reducing agent. Examples of such reducing agents include, but are not limited to, aluminum hydrides and borohydrides (e.g. $BH_3$, $AlH_3$, $LiBH_4$, $LiAlH_4$, $NaBH_4$, $NaAlH_4$, $ZnBH_4$).

The hydroxyl group of compound 2-4 may be transformed to a leaving group such as but not limited to a sulfonate (e.g., MsO—, TsO—, TfO—) or halide by methods described in the literature. Subsequent treatment with a cyanide source (e.g., KCN or NaCN) results in the formation of compound 2-5.

Alternatively, compound 2-4 may be transformed to compound 2-5 by oxidation of the hydroxyl group to the aldehyde by methods described in the literature. Conversion of the aldehyde to the nitrile may be achieved with appropriate reagents such as, but not limited to, dimethyl phosphorocyanidate/samarium iodide. Compound 2-5 may be alkylated in an appropriate solvent, e.g., an aprotic solvent such as tetrahydrofuran, toluene, TBME and subsequently treated with a strong base such as a metal amide or metal alkoxides (e.g., LDA, KHMDS, or KO$^t$Bu) and an appropriate alkyl halide (e.g., X-Me) or sulfonate to provide a compound of formula (Ib).

Alternatively, compound 2-1 may be converted to compound 2-7 by methods known in the art. Examples of such methods include, but are not limited to, treatment with N,O-dimethylhydroxylamine hydrochloride/trimethylaluminum. Compound 2-7 can be converted into the compound of formula (Id), by treatment with an appropriate carbon-nucleophile. Examples of such nucleophiles include, but are not limited to, alkyl Grignard reagents.

Alternatively, oxidation of compound 2-4 to the aldehyde followed by addition of an alkyl Grignard or other carbon-nucleophile provides a secondary alcohol. Oxidation using known methods results in the formation of the compound of formula (Id). Compounds of formula (Ib) may be synthesized, for example, by the treatment of the compound of formula (Id) with TosMIC in the presence of metal alkoxides, such as NaOEt and KOtBu (J. Org. Chem. 42(19), 3114-3118, (1977)). Alternatively, the compound of formula (Id) may be transformed to the compound of formula (Ib) using reagents such as but not limited to dimethyl phosphorocyanidate/samarium iodide.

Conversion of (−)-Quinic Acid to a Compound of Formula (Id)

Alternatively a compound of formula (Id) may also be synthesized as shown in Scheme 3.

Scheme 3

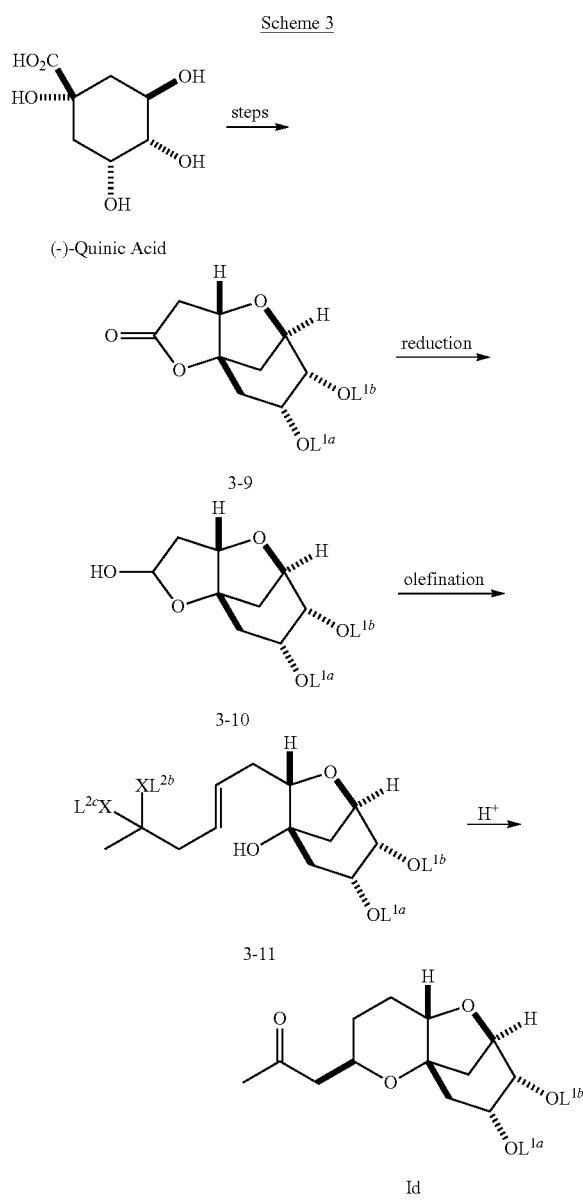

In Scheme 3, $L^{1a}$ and $L^{1b}$ are protecting groups, as described in Scheme 2. $L^{2b}$ and $L^{2c}$ are also protecting groups such as, but not limited to, cyclic acetals (X=O and/or S), cyclic ketals (X=O and/or S), and cyclic carbonates (X=O).

The synthesis of compound 3-9 from commercially available (−)-quinic acid has been described previously (WO/ 2005/118565). Compound 3-9 may be reduced with DIBAL or other reagents known in the art, such as aluminum hydrides and borohydrides, to provide lactol 3-10. The lactol 3-10 can be transformed using a Wittig or Julia olefination to provide compound 3-11. Deprotection followed by double bond migration and Michael addition generate compound (Id).

More specifically, a Wittig olefination may be carried out using $MeC(OL^{2b})(OL^{2c})CH_2CH_2PPh_3$ (prepared in situ), in a polar solvent (e.g., THF, MeOH, or DMF) at a temperature ranging from 0° C. to 50° C. Acid-catalyzed sequential reactions (e.g., deprotection, migration, and Michael addition) may be carried out with an acid such as TsOH or HCl in a polar solvent (e.g. THF, or acetone) at a temperature ranging from 10 to 30° C. for about two to four hours. Alternatively, the migration and Michael addition may also be carried out with a base such as NaOMe in a polar solvent (e.g., THF or MeOH).

Conversion of Compound 4-1 to a Compound of Formula (I)

As shown in Scheme 4, compounds of formula 4-1 (diastereomeric mix) may undergo isomerization and crystallization to provide compounds of formula (I).

Scheme 4

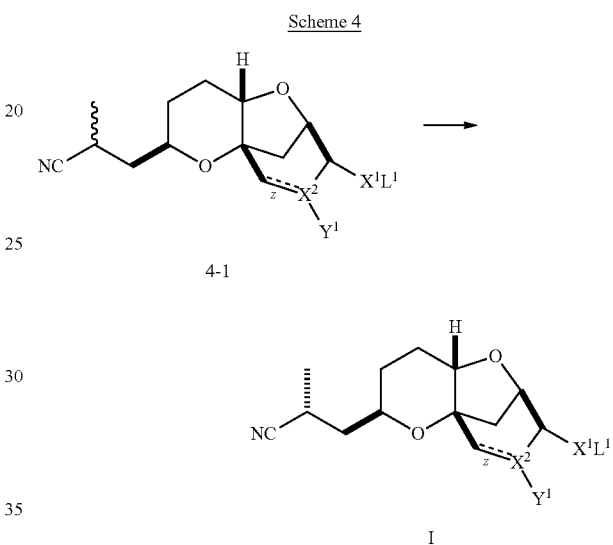

In Scheme 4, z is a single or double bond, provided that when z is a double bond, $X^2$ is C and $Y^1$ is hydrogen; and provided that when z is single bond, $X^2$ is CH or O; $X^1$ is O, S, or CN, provided that when $X^1$ is CN or S, $X^2$ is O; $Y^1$ is a halide, hydrogen or $O-L^2$, or absent when $X^2$ is O; and $L^1$ and $L^2$ are independently selected from hydrogen and a protecting group, or $L^1$ and $L^2$ together are a protecting group, provided that when $X^1$ is CN, $L^1$ is absent.

Diastereomers of formula 4-1 may be converted to compounds of formula (I) via treatment with sub-stoichiometric amounts of amide bases (e.g., KHMDS) at low temperatures (e.g., less than about −30° C.). Once quenched, compounds of formula (I) may be isolated and recrystallized from a suitable crystallization solvent systems, such as, but not limited to, heptane/t-butyl methyl ether and heptane/isopropanol.

Alternatively a crystallization induced dynamic resolution (CIDR) may also be used to selectively crystallize compounds of formula (I). For example, diastereomers of formula 4-1 may be treated with a base, such as an alkoxide, (e.g., t-butyl oxide or isopropoxide) in an appropriate crystallization solvent system. Examples of appropriate crystallization solvent systems include combinations of a protic solvent (e.g., isopropanol) and an anti-solvent (e.g., heptane) at non-cryogenic temperatures to provide purified compounds of formula (I).

Conversion of a Compound of Formula (Ib) to Compound 5-13

Conversion of Compound 5-13 to Compound 6-16

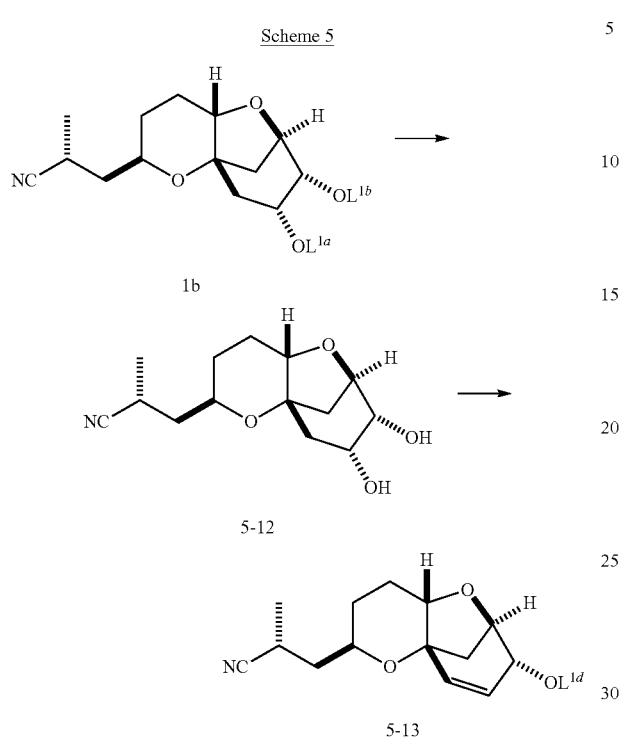

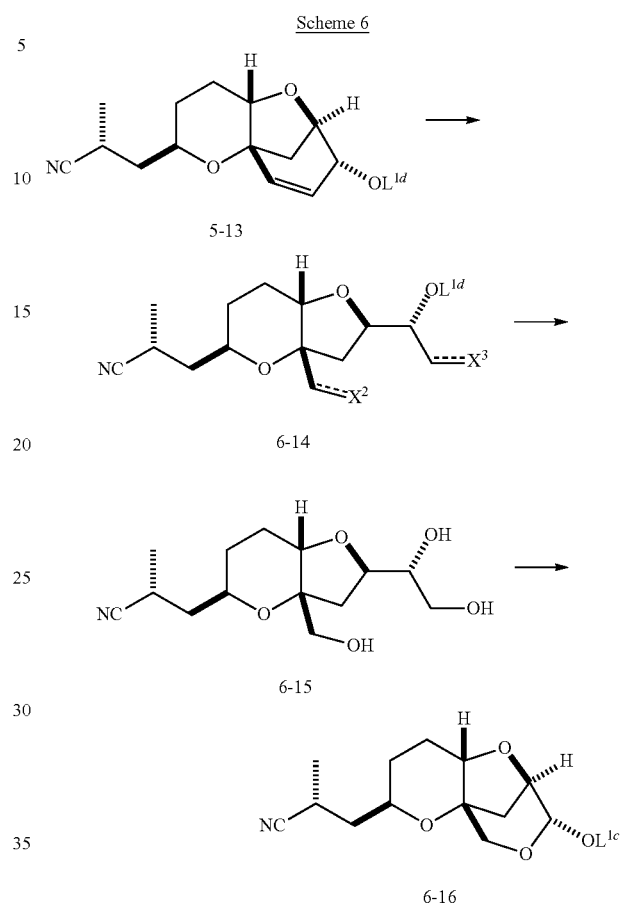

In Scheme 5, $L^{1a}$ and $L^{1b}$ are as described above in Scheme 2. $L^{1d}$ is a suitable protecting group, e.g., $C_1$-$C_6$ alkyl ether, aryl ($C_1$-$C_6$) alkyl ether, $C_1$-$C_6$ ester, or a silyl ($C_1$-$C_{10}$) ether.

Compounds of formula (Ib) may be deprotected by various methods known in the art, depending on the nature of $L^{1a}$ and $L^{1b}$. Examples of deprotecting reactions include, but are not limited to hydrogenation, reduction, oxidation, base induced deprotection, and acid induced deprotection. One of ordinary skill in the art would be able to choose an appropriate technique based on art recognized techniques (see, e.g., Protective Groups in Organic Synthesis, 3$^{rd}$ edition, John Wiley & Sons, Inc).

Once $L^{1a}$ and $L^{1b}$ have been removed, the deprotected compound 5-12 may be converted to compound 5-13 by treatment of compound 5-12 with 2-acetoxy-2-methylpropionyl bromide, catalytic water, in a polar aprotic solvent such as acetonitrile. The resulting intermediate may be treated with a base (e.g., diazabicycloundecane (DBU)) to provide compound 5-13.

Alternatively, compound 5-12 may be transformed to compound 5-13 using a multi-step process. The process involves selectively activating of one hydroxyl group as a halide, MsO—, TsO—, or TfO— and protecting of the remaining hydroxyl group. Examples of suitable protecting groups for this step include $L^{1d}$ groups such as $C_1$-$C_6$ alkyl ethers, aryl ($C_1$-$C_6$) alkyl ethers, $C_1$-$C_6$ esters, and silyl ($C_1$-$C_{10}$) ethers. The intermediate can be transformed to compound 5-13 using methods described previously.

In Scheme 6, $L^{1d}$ is hydrogen or a protecting group, $C_1$-$C_6$ alkyl ether, aryl ($C_1$-$C_6$) alkyl ether, $C_1$-$C_6$ ester, or a silyl ($C_1$-$C_{10}$) ether). $L^{1c}$ may be hydrogen or a protecting group, such as, but not limited to a glycoside, $C_1$-$C_6$ alkyl, or a $C_1$-$C_6$ ester. $X^2$ and $X^3$ may each be oxygen or hydroxy.

Oxidative cleavage of the olefin of compound 5-13 may be accomplished using ozone in a suitable solvent (e.g., methanol) at temperatures below 0° C. The ozone adduct may worked up using literature methods to provide compound 6-14, wherein $X^2$ and $X^3$ are each carbonyl or hydroxy. Alternatively, a metal oxide (e.g., osmium tetroxide or potassium permanganate and sodium periodate) may also be used to provide compound 6-14, wherein $X^2$ and $X^3$ are each carbonyl.

When $X^2$ and $X^3$ are each carbonyl, they can be reduced to provide compound 6-14, wherein $X^2$ and $X^3$ are each hydroxy. Deprotection of $L^1$ may be achieved using literature methods (e.g., potassium carbonate in methanol) to provide compound 6-15. Compound 6-15 may be treated with $NaIO_4$ to provide compound 6-16, wherein $L^{1c}$ is H. Alternatively, compound 6-16 may comprise a glycoside (e.g., $L^{1c}$ is $C_1$-$C_3$ alkyl, e.g., methyl) protecting group which can be added using methods known in the art, such as methanol in the presence of an acid catalyst.

Conversion of Compound 2-1 to Compound 6-16

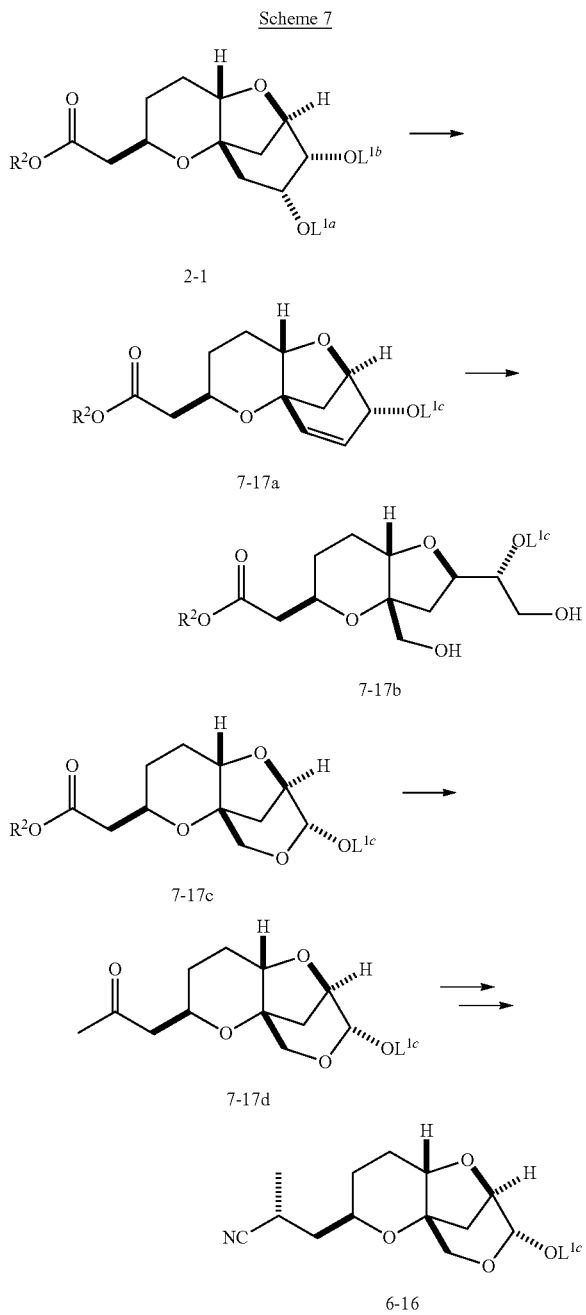

Conversion of Compound 5-16 to Compound 7-20

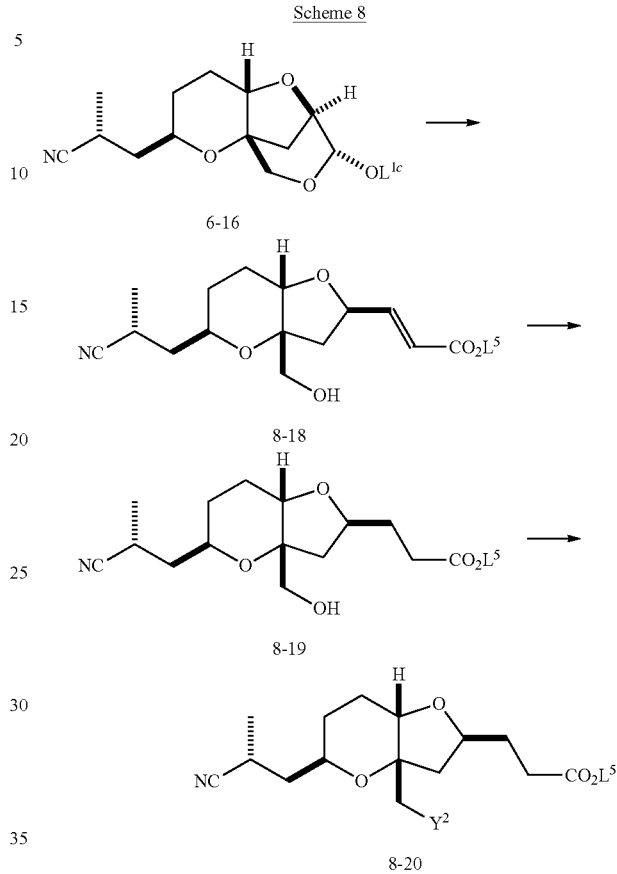

In Scheme 7, an alternate route to compound 6-16 is shown. Examples of $R^2$ include hydrogen, $C_1$-$C_6$ alkyl (e.g., methyl, t-butyl, etc.), $C_4$-$C_{10}$ aryl (e.g., phenyl), and $C_4$-$C_{10}$ aryl-$C_1$-$C_6$ alkyl groups (e.g., benzyl). $L^{1a}$ and $L^{1b}$ are protecting groups as described above. Examples of $L^{1e}$ include hydrogen and protecting groups such as glycosides, $C_1$-$C_6$ alkyl and $C_1$-$C_6$ acetyl. Compound 2-1 may be transformed to compound 7-17d as described in Schemes 5 and 6. Treatment of compound 7-17d with TosMIC and isomerization/crystallization provides compound 6-16, as shown in Schemes 2 and 4.

Compound 8-20 may be prepared from 6-16 as shown in Scheme 8. In Scheme 8, $L^{1c}$ is hydrogen or a protecting group as described previously; $L^5$ is $C_1$-$C_{10}$ alkyl, $C_4$-$C_{10}$ aryl-$C_1$-$C_6$ alkyl, or $C_4$-$C_{10}$ aryl; and $Y^2$ is sulfonate or halide.

When $L^{1e}$ is not hydrogen, the ether is hydrolyzed using literature methods to provide lactol (6-16, $L^{1c}$=H). The lactol (6-16, $L^{1c}$=H) is converted to compound 8-18 by an olefination reaction such as a stabilized Wittig reaction, a Wadsworth-Horner-Emmons reaction, or a Julia olefination. The Wittig olefination may be carried out with a stabilized ylide such as $Ph_3PCHCO_2L^3$ in polar solvent (e.g., THF, MeOH, or DMF) at an appropriate temperature (e.g., -78° C. to 50° C.). The Wadsworth-Horner-Emmons olefination may be carried out using a stabilized ylide (e.g. $(MeO)_2POCH_2CO_2L^5$) in a polar aprotic solvent (e.g., THF, or ACN) at an appropriate temperature (e.g., -78° C. to 25° C.) in the presence of a suitable base (e.g., $^t$BuOK, NaH, or LiCl/tertiary amines (e.g. DBU, $^i$Pr$_2$NEt, Et$_3$N)).

Variations on these conditions are known in the art. For example, for variations on the Wadsworth-Horner-Emmons olefination see Org. React. 25, 73-253, (1977) and Tetrahedron Lett. 25, 2183 (1984). Furthermore, the Julia olefination may be carried out in a polar aprotic solvent (e.g., THF, DME or a halogenated solvent, e.g., $CH_2Cl_2$) in the presence of alkyl sulfone (e.g., alkyl(benzothiazol-2-ylsulfonyl)acetate) and suitable base (e.g., BuLi, LDA, KHMDS, or DBU) at an appropriate temperature (e.g., -78° C. to 25° C.). Variations on these conditions will be apparent from the literature on Julia olefination (see, Org. Biomol. Chem. 3, 1365-1368, (2005); Synlett, 26-28, (1998)).

Compound 8-19 can be obtained from compound 8-18 via catalytic hydrogenation, which may be carried out in the presence of a metal catalyst (e.g., palladium (Pd/C) or platinum ($PtO_2$)) in a polar solvent (e.g. EtOAc, MeOH). Preferably, the reaction is carried out under a hydrogen atmosphere, with a pressure ranging from 0.04 bar to 1.10 bar.

The hydroxyl group of 8-19 may be converted to a leaving group (e.g., MsO—, TsO—, TfO—) providing 8-20, using a suitable sulfonyl anhydride or sulfonyl chloride (e.g., MsCl, TsCl, or $Tf_2O$) in a polar aprotic solvent (e.g., THF or a halogenated solvent (e.g., $CH_2Cl_2$)), in the presence of a suitable base (e.g., $Et_3N$).

Optionally, the leaving group of 8-20 may be converted to a halide. This reaction may be carried out in the presence of a halogenating reagent (e.g., NaI, or NaBr) in a polar solvent (e.g., DMF or acetone). Alternatively, the transformation of hydroxyl group to halide may be carried out using a halogenating reagent (e.g., NIS, or NBS) in a polar solvent (e.g., THF) in the presence of $Ph_3P$ and a suitable base such as pyridine.

Conversion of Compound 6-15 to Compound 8-20

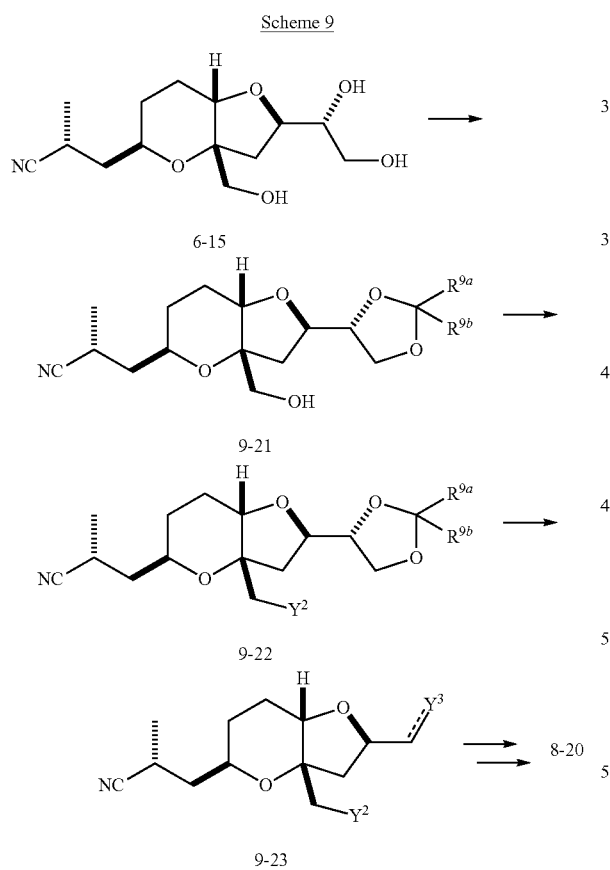

In Scheme 9, another method of converting compound 6-15 to compound 8-20 is shown. In Scheme 9, $R^{9a}$ and $R^{9b}$ are hydrogen, $C_1$-$C_6$ alkyl or taken together are a carbonyl group; $Y^2$ is sulfonate or halide; and $Y^3$ is O, $OL^3$, or $CHCO_2$-$L_3$ wherein $L^3$ is hydrogen or a protecting group.

As shown in Scheme 9, compound 8-20 can be prepared from compound 6-15 using literature methodology for the protection of 1,2 diols. Treatment of the neopentyl-hydroxyl of compound 9-21 (using methods described in Scheme 8) provides compound 9-22. Deprotection of the compound 9-22 using literature methods provides a diol. Treatment of this diol with a reagent such as sodium periodate provides aldehyde 9-23 ($Y^3$=O). Treatment of the aldehyde 9-23 as described in Scheme 8 provides compound 8-20.

Conversion of Compound 7-17b to 8-20

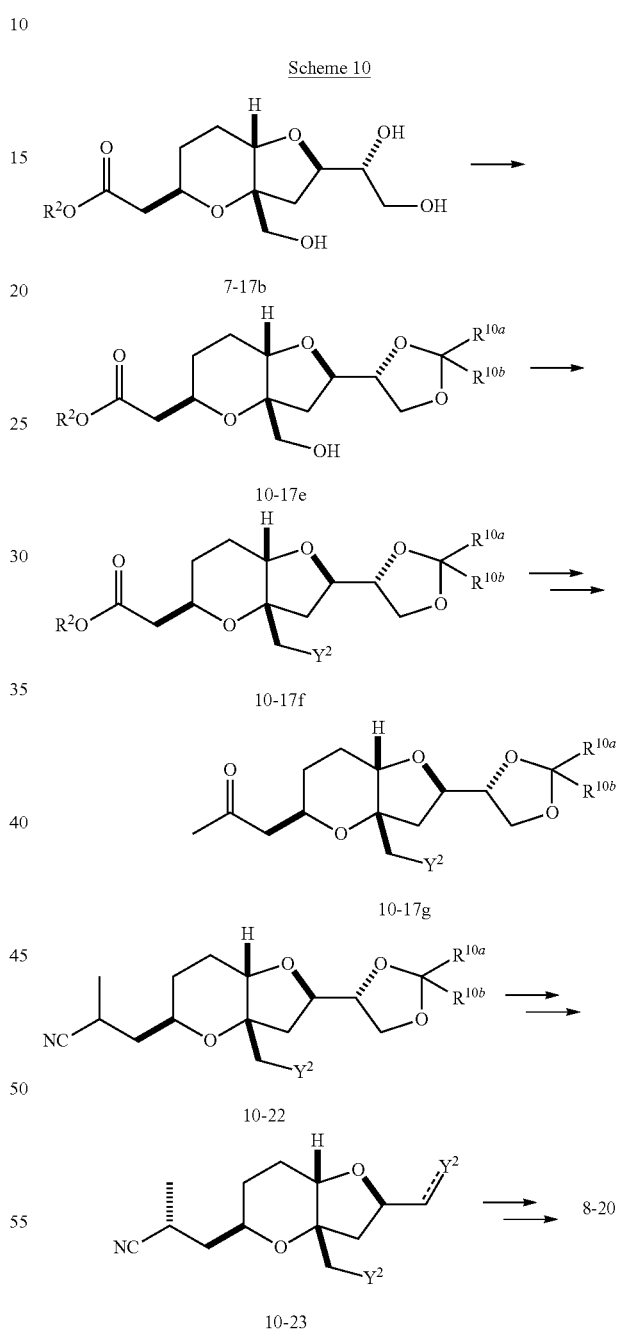

Alternatively, compound 7-17b may be converted to compound 8-20 as shown in Scheme 10. In Scheme 10, $R^2$ includes $C_1$-$C_6$ alkyl such as methyl, ethyl, and tert-butyl; $R^{10a}$ and $R^{10b}$ are hydrogen, $C_1$-$C_6$ alkyl or taken together are a carbonyl group; $Y^2$ is sulfonate or halide; and $Y^3$ is O, $OL^3$, or $CHCO_2$-$L_3$. $L^3$ is hydrogen or a protecting group.

Compound 7-17b may be transformed into compound 10-17f by selectively protection of the 1,2-diol and a subsequent functional group transformation of the neopentyl hydroxyl group to a sulfonate or halide. Selective protection of 1,2-diol may be carried out with an aldehyde, ketone, acetal, or a carboxyl chloride (e.g. DMP, cyclohexanone, MeOPhCHO, or Ph$_3$P) in the presence of acid catalyst. The functional group transformation of the neopentyl hydroxyl group to a sulfonate or halide has been previously described above in Scheme 8. Compound 10-17g and 10-22 may be prepared in a similar manner previously described in Scheme 2. Deprotection of the diol protecting group using literature procedures followed by treatment with sodium periodate provides 10-23 (Y=O). A Wittig, Horner-Wadsworth-Emmons, or Peterson type olefination is then followed with hydrogenation to provide compound 8-20.

D. Chemical Examples

Example 1: Synthesis of Compound AD from Compound AC

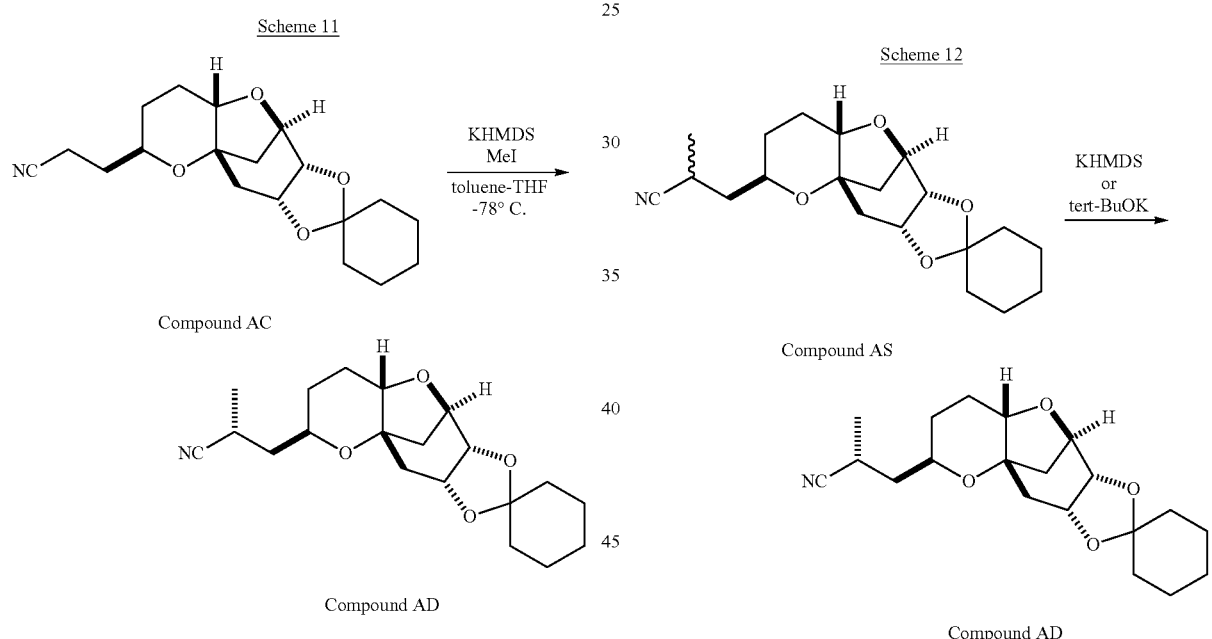

Example 2: Diastereomeric Purification of Compound AD from Compound AS

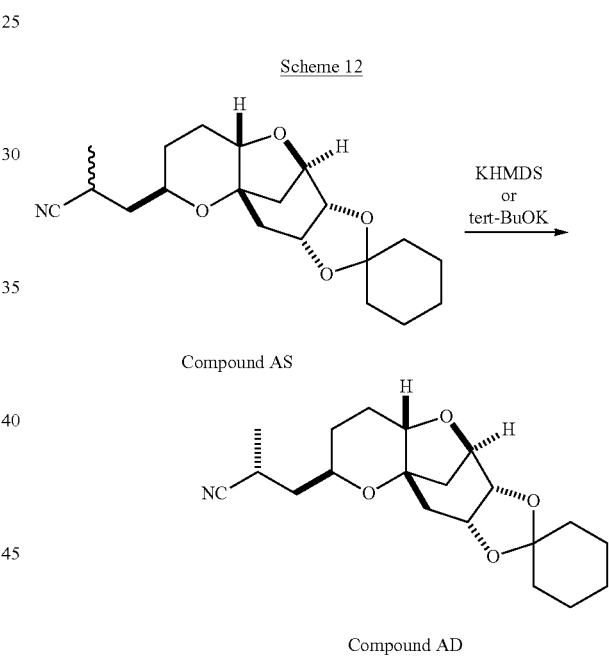

Compound AC (1 Wt, 1 V, 1 eq) was dissolved in THF (1.80 V) and cooled to −75° C. KHMDS (0.50M solution in toluene, 6.60 V, 1.10 eq) was added at a rate such that internal temperature did not exceed −65° C. Upon complete addition, stirring was continued at −75° C. for 30 minutes. A solution of MeI (0.188 V, 1.01 eq) in THF (0.50 V) was added at a rate such that internal temperature did not exceed −65° C. Upon complete addition, stirring was continued at −75° C. for 1 hour. KHMDS (0.50M solution in toluene, 0.60 V, 0.10 eq) was added at a rate such that internal temperature did not exceed −70° C. and stirring was continued at −75° C. for additional 2.5 hours. Under vigorous stirring, 20 wt % NH$_4$Cl aq (1.50 Wt, 1.9 eq) was added at a rate such that internal temperature did not exceed −55° C. Upon complete addition, the resultant mixture was allowed to warm to −20° C. Water (1.50 V) was added and the mixture was further warmed to 0° C. The biphasic mixture was transferred to a work-up vessel (the reactor was washed with MTBE (0.40 V)) and vigorous stirring was continued for 2 minutes. The aqueous layer was set aside and the organic layer was washed with water (2.0 V). The organic layer was concentrated and residual solvents and water were azeotropically removed with heptane (1.50 V×2) to give the crude product as a yellow solid (1.1 Wt, dr=4.4:1).

The crude (1.1 Wt) was suspended in heptane-MTBE (4:1 v/v, 5.0 V) and heated to 80° C. The resultant solution was: 1) cooled to 70° C. over 1 hour; 2) held at 70° C. for 0.5 hour; 3) cooled to 65° C. over 0.5 hour (precipitation started); 4) held at 65° C. for 0.5 hour; 5) cooled to 60° C. over 0.5 hour; 6) held at 50° C. for 0.5 hour; 7) cooled to room temperature and stirring was continued for 40 hours. Crystals were collected by filtration, washed with heptane (1 V×2) and dried under N$_2$/vacuum to give Compound AD as light tan powder (0.69 Wt, 0.66 eq, dr=34:1). The mother liquor was concentrated to give an epimeric mixture (Compound AS) as yellow solid (epimeric mixture, 0.38 Wt, dr Compound AD:epimer=1:2.2).

Each of the following methods was used in the reaction shown in Scheme 12 to convert the undesired C25 epimer to the desired C25 isomer, using either stereoselective deprotonation-protonation or crystallization induced dynamic resolution (CIDR).

Method 1: Compound AS (1 Wt, 1 V, dr=1:2.2) was dissolved in toluene (2.6 V) and cooled to −20° C. KHMDS (0.50 M solution in toluene, 3.4 V, 0.60 eq) was added at a rate such that internal temperature did not exceed −16° C. Upon complete addition, stirring was continued at −20° C. for 15 minutes. Under vigorous stirring, 20 wt % NH$_4$Cl aq (1.0 Wt, 1.3 eq) was added at a rate such that internal temperature did not exceed −15° C. After 5 minutes, the mixture was allowed to warm to 0° C. The organic layer was separated, washed with water (2.0 V) and concentrated. The residual solvents and water were azeotropically removed with heptane (3.0 V×2) to give the crude product as yellow solid-oil mixture (dr=2.6:1). The crude was suspended in Heptane-MTBE (5:1, v/v, 3.0 V) and heated to 80° C. The resultant clear solution was cooled to room temperature (23° C.) over 3 hours (precipitation started at 45° C.). The crystals were collected by filtration, washed with: 1) heptane-MTBE (5:1 v/v, 1.0 V); 2) heptane (1.0 V) and dried under N$_2$/vacuum to give Compound AD as white powder (0.31 Wt, 0.31 eq, 0.08 eq). The mother liquor was concentrated to give Compound AS (0.69 Wt, dr=1:1).

Method 2: Compound AS (1 Wt, 1 V, dr=1:1) was dissolved in heptane-MTBE (5:1 v/v, 2.0 V) and KHMDS (0.50 M solution in toluene, 0.40 V, 0.07 eq) was added at 23° C. Stirring was continued for 10 minutes and the mixture was cooled to 0° C. Compound AD (0.0001 Wt, 0.0001 eq) was added and stirring was continued for an additional 30 minutes (precipitation increased). 20 wt % NH$_4$Cl aq (0.20 Wt, 0.26 eq) was added under vigorous stirring. The resultant mixture was diluted with EtOAc (2.0 V) to dissolve Compound AD precipitation. The organic layer was separated, washed with water (1.0 V) and concentrated. The residual solvents and water were azeotropically removed with heptane (5 V×2) to give crude product as yellow solid-oil mixture (dr=2.3:1). The crude was suspended in heptane-MTBE (3:1 v/v, 1.5 V) and heated to 80° C. The resultant clear solution was cooled to 20° C. over 3 hours (precipitation started at 50° C.). The crystals were collected by filtration, washed with heptane-MTBE (4:1 v/v, 1 V), and dried under N$_2$/vacuum to give Compound AD as white powder (0.22 Wt, 0.22 eq, 0.04 eq).

Method 3 (CIDR): Compound AS (1 Wt, 1 V, dr=1:5) was dissolved in heptane (5 V) at 23° C. t-BuOK (1.0 M solution in THF, 0.29 V, 0.10 eq) was added and stirring was continued for 10 minutes. The precipitations were collected by filtration, washed with heptane (10 V), and dried to give Compound AD as light tan powder (0.36 Wt, 0.36 eq, dr=7.3:1, filtrate dr=3.7:1).

Method 4: Compound AS (1 Wt, 1 V, 1 eq, dr=1:1.7) was dissolved in toluene (5.0V) and cooled to −70~−75° C. KHMDS (0.5M solution in toluene, 0.500 eq, 2.88 V, 2.53 Wts) was added while maintaining an internal temperature below −65° C. The resultant mixture was cooled to −70~−75° C. again and stirring was continued at −70~−75° C. for 4 hours. 20 wt % NH$_4$Cl (aqueous solution, 2.00 Wts) was added while maintaining an internal temperature below −60° C. Upon complete addition, the mixture was allowed to warm to 0° C. over a period of 1.5~2 hours. MTBE (4.00 V, 2.96 Wt) and water (4.00 V, 4.00 Wt) were added under stirring and the resultant biphasic mixture was allowed to partition. Organic layer (dr=6.5:1) was separated, sequentially washed with: 1) 20 wt % citric acid (aqueous solution, 1.0 Wt); 2) water (3.00 V); 3) water (3.00 V) and partially concentrated to ~2V under vacuum. The residue was subjected to solvent exchange with heptane (6.00 V×2, partial concentration to ~2V each time, under vacuum) and diluted with heptane-IPA (6:1 v/v, 3.5V). The mixture was heated to 60° C., cooled to 15~20° C. over 4 hours, and further stirred at 15~20° C. overnight. Crystals were collected by filtration, rinsed with heptane-IPA (9:1 v/v, 2.0 V) and dried under N$_2$/vacuum to give Compound AD (0.4 Wt, 0.4 eq, dr=57:1) as light tan powder.

$^1$H NMR (500 MHz, CDCl$_3$)

δ 4.40-4.44 (1H, m), 4.30 (1H, dd, J=6.5, 3.5 Hz), 4.09 (1H, dd, J=6.5, 3.0 Hz), 3.72-3.77 (1H, m); 3.37 (1H, dd, J=10.0, 6.5 Hz), 2.91-2.99 (1H, m), 2.35-2.39 (1H, m), 2.07-2.12 (1H, m), 1.97-2.03 (1H, m), 1.96 (1H, dd, J=14.0, 4.0 Hz), 1.82 (1H, d, J=12.0 Hz), 1.58-1.70 (5H, m), 1.50-1.58 (6H, m), 1.42-1.49 (1H, m), 1.32-1.40 (2H, m), 1.29 (3H, d, J=7.0 Hz), 1.11-1.20 (1H, m)

$^{13}$C NMR (125 MHz, CDCl$_3$) δ 122.95, 110.58, 78.29, 76.28, 75.92, 75.81, 72.16, 68.34, 43.80, 40.51, 37.61, 34.52, 29.85, 28.92, 27.24, 25.33, 24.24, 23.84, 22.50, 18.55

LRMS (ESI) m/z found 370.15 [M+Na]$^+$

Melting Point 123° C.

Example 3: Synthesis of Compound AJ from Compound AD

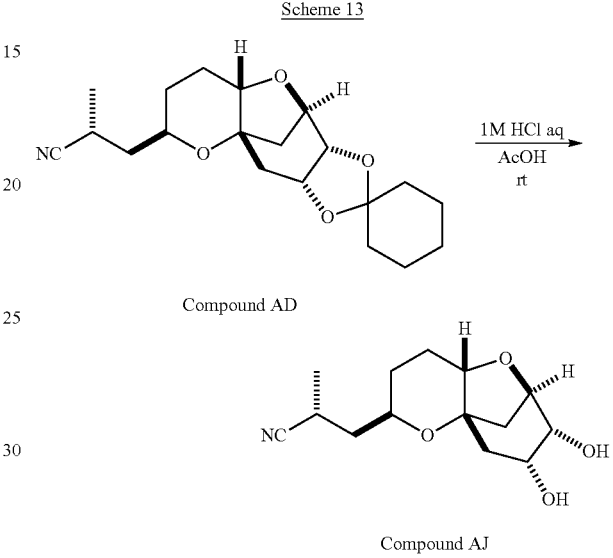

Scheme 13

Compound AD

Compound AJ

Compound AD (1 Wt, 1 V) was suspended in AcOH (5.00 V, 31 eq) at 20° C. 1.00 M HCl aq (2.48 V, 1.00 eq) was added and stirring was continued at 20° C. for 5 hours. The reaction mixture was cooled to 0° C. and 50 wt % NaOH aq (2 Wt, 8 eq) was added while maintaining internal temperature below 10° C. Heptane-MTBE (2:1 v/v, 10.0 V) was added and vigorous stirring was continued for 3 minutes. The organic layer was set aside and the aqueous layer was extracted with acetonitrile (10.0 V×2). All of the acetonitrile layers were combined, washed with brine (2.0 V) and concentrated. The residual solvents were azeotropically removed with acetonitrile (8.0 V×2) to give the crude product as yellow solid (0.62 Wt, 0.080 eq).

Crude Compound AJ (1 Wt, 1 V) was suspended in IPA (6.0 V) and heated to 80° C. The resultant solution was cooled to room temperature over 1 hour. The mixture was further cooled to 0° C. and stirring was continued at 0° C. for an additional hour. The precipitations were collected by filtration, washed with cold IPA (2.0 V), and dried to give Compound AJ as a white powder (0.72 Wt, 0.72 eq).

$^1$H NMR (500 MHz, CDCl$_3$)

δ 4.37 (1H, dd, J=6.5, 5.0 Hz), 3.97-4.04 (1H, m), 3.88-3.89 (1H, m), 3.74-3.79 (1H, m), 3.42 (1H, dd, J=10.0, 7.0 Hz), 2.91-2.99 (1H, m), 2.56 (1H, br), 2.37-2.41 (1H, m), 2.27 (1H, br), 2.05-2.11 (1H, m), 1.96-2.00 (1H, m), 1.82 (1H, d, J=11.5 Hz), 1.75 (1H, t, J=11.5 Hz), 1.65-1.70 (1H, m), 1.54-1.61 (2H, m), 1.47-1.53 (1H, m), 1.32 (3H, d, J=7.0 Hz), 1.15-1.24 (1H, m)

$^{13}$C NMR (125 MHz, CDCl$_3$)

δ 122.93, 77.71, 77.00 (overlapped with chloroform signal), 73.60, 69.14, 68.45, 67.04, 43.66, 40.38, 29.88, 28.85, 28.37, 22.48, 18.53

13C NMR (125 MHz, acetone-d6)

δ 122.60, 77.77, 77.04, 73.32, 69.40, 68.34, 66.55, 44.02, 40.11, 29.93, 28.74, 28.16, 22.25, 17.95

LRMS (ESI) m/z found 289.95 [M+Na]+

Melting Point 189° C.

Example 4: Synthesis of Compound AK from Compound AJ

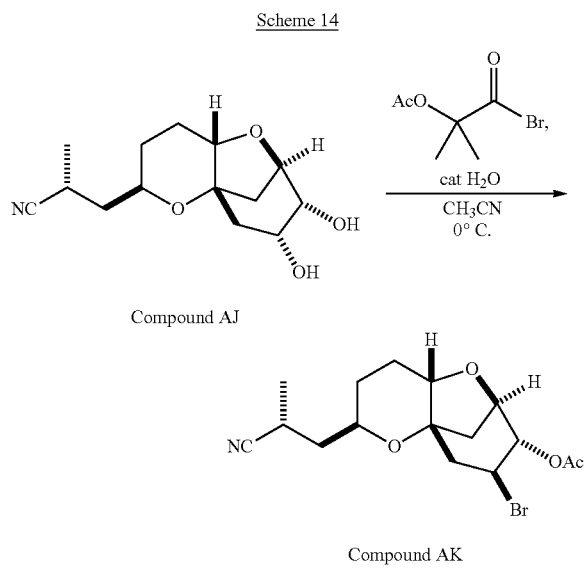

Compound AJ (1 Wt, 1 V, 1 eq) was suspended in acetonitrile (5.00 V) and cooled to 0° C. 2-acetoxy-2-methylpropionyl bromide (0.938 Wt, 0.656 V) was added at a rate such that the internal temperature did not exceed 7° C. Upon complete addition, water (0.002 V, 3 mol %) was added and stirring was continued at 0° C. for an additional hour. The reaction mixture was diluted with MTBE (5.0 V). After internal temperature dropped to 0° C., 10 wt % NaHCO3 aq (5.0 V, 3.4 eq) was carefully added under vigorous stirring maintaining internal temperature below 7° C. and the resultant mixture was allowed to partition. The organic layer was set aside and the aqueous layer was extracted with MTBE (5.0 V). All of the organic layers were combined, sequentially washed with: 1) 10 wt % NaHCO3 aq (2.0 V, 1.4 eq); 2) water (2.0 V); 3) brine (2.0 V), and concentrated to give crude Compound AK as light brown oil (1.47 Wt, 1.04 eq). The crude product was azeotropically dried with toluene (4 V×3) and used for next reaction without purification.

1H NMR (500 MHz, CDCl3)

δ 5.20 (1H, br), 4.38 (1H, dd, J=6.5, 3.5 Hz), 4.21-4.23 (1H, m), 4.04 (1H, dd, J=10.0, 7.0 Hz), 3.79-3.83 (1H, m), 2.90-2.98 (1H, m), 2.51-2.56 (2H, m), 2.30-2.34 (1H, m), 2.11-2.15 (1H, m), 2.07 (3H, s), 1.65-1.71 (1H, m), 1.57-1.62 (3H, m), 1.49-1.55 (1H, m), 1.32 (3H, d, J=6.5 Hz), 1.21-1.30 (1H, m)

13C NMR (125 MHz, CDCl3)

δ 169.39, 122.79, 78.13, 75.49, 75.42, 73.76, 68.45, 44.66, 43.48, 40.11, 29.48, 28.88, 28.38, 22.40, 21.12, 18.46

LRMS (ESI) m/z found 393.96 [M+Na]+

Example 5: Synthesis of Compound AL from Compound AJ

Scheme 15

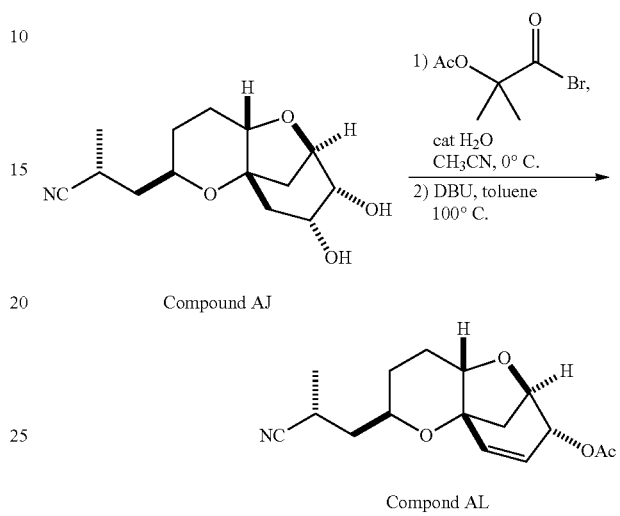

Compound AJ (1 Wt, 1 V, 1 eq) was suspended in acetonitrile (3.0 V) and cooled to 0° C. 2-acetoxy-2-methylpropionyl bromide (1.02 Wt, 1.30 eq) was added at a rate such that the internal temperature did not exceed 2° C. Upon complete addition, an acetonitrile-water mixture (water (0.0020 V, 0.030 eq) and acetonitrile (0.020 V)) were added and stirring was continued at 0° C. for 2 hours. Under vigorous stirring, 10 wt % NaHCO3 aq (5.0 V) was added at a rate such that the internal temperature did not exceed 8° C. (CO2 evolution). Toluene (4.3 Wt, 5.0 V) was added and vigorous stirring was continued for 3 minutes. The mixture was allowed to partition and the organic layer was set aside. The aqueous layer was extracted with toluene (2.6 Wt, 3.0 V). All of the organic layers were combined and sequentially washed with: 1) 10 wt % NaHCO3 aq (3.0 V); 2) water (2.0 V).

The organic layer was transferred to a reactor and subjected to distillation under atmospheric pressure to remove 5 Wt of solvent. The distillation included heating the organic layer to 90° C. to remove the acetonitrile and then heating the mixture to about 110° C. to remove the toluene. After cooling to 80° C., toluene (2.50 Wt, 3 V) was added followed by DBU (1.12 V, 1.14 Wt, 2.00 eq). The mixture was re-heated to 100° C. and vigorously stirred for 17 hours. The reaction mixture was cooled to 0° C. and 1.00 M HCl aq (4.5 V, 1.2 eq) was added at a rate such that the internal temperature did not exceed 8° C. The resultant mixture was allowed to partition. The organic layer was set aside and aqueous layer was extracted with toluene (1.73 Wt, 2.0 V). All of the organic layers were combined, sequentially washed with: 1) 1.00 M HCl aq (0.50 V, 0.13 eq); 2) 10 wt % NaHCO3 aq (1.0 V); 3) water (2.0 Wt, 2.0 V), and concentrated. The residual toluene was azeotropically removed with IPA (2.0 V) to give the crude product as yellow solid. Crude Compound AL was suspended in IPA (5.0 V) and heated to 80° C. The resultant solution was cooled to 0° C. over 2 hours and stirring was continued at 0° C. for an additional 30 minutes. Crystals were collected by filtration, washed with cold IPA (1 V) followed by heptane (1 V), and dried to give Compound AL as white powder (0.64 Wt, 0.59 eq). The mother liquor was concentrated and diluted with IPA-heptane (1:1 v/v, 1.0 V). A white precipitation was formed, collected by filtration, washed with: 1) IPA-heptane (1:1 v/v, 0.4 V); 2) heptane (0.4 V), and dried to give additional Compound AL (0.043 Wt, 0.040 eq).

Example 6: Synthesis of Compound AL from Compound AK

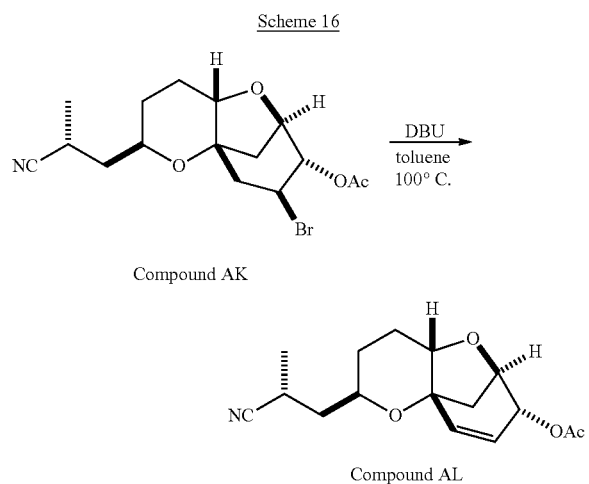

Scheme 16

Compound AK

Compound AL

Compound AK (1 Wt, 1 V, 1 eq) was dissolved in toluene (5.0 V). DBU (0.818 Wt, 0.803 V, 2.0 eq) was added at 23° C. and the mixture was heated to 100° C. Upon complete consumption of Compound AK, the reaction mixture was cooled to 10° C. and 1M HCl (3.5 V, 1.3 eq) was added. The resultant mixture was vigorously stirred for 5 minutes and allowed to partition. The organic layer was set aside and the aqueous layer was extracted with MTBE (5.0 V). All organic layers were combined, sequentially washed with: 1) water (2.0 V); 2) 10 wt % NaHCO$_3$ solution (2.0 V); 3) water (2.0 V), and concentrated to give a mixture of light brown oil and water. The residual water was azeotropically removed with heptane (3.0 V×3) to give crude Compound AL as yellow solid (0.65 Wt, 0.83 eq)

$^1$H NMR (500 MHz, CDCl$_3$)

δ 6.16 (1H, d, J=10 Hz), 5.60-5.63 (1H, m), 5.01-5.02 (1H, m), 4.34-4.36 (1H, m), 3.80-3.85 (1H, m), 3.42 (1H, dd, J=5.0, 2.0 Hz), 2.93-3.01 (1H, m), 2.53-2.57 (1H, m), 2.07-2.12 (1H, m) 2.03 (3H, s), 1.56-1.72 (4H, m), 1.49-1.55 (1H, m), 1.32 (3H, d, J=6.5 Hz), 1.22-1.30 (1H, m)

$^{13}$C NMR (125 MHz, CDCl$_3$)

δ 170.10, 142.16, 122.82, 122.42, 79.43, 75.26, 74.81, 69.52, 68.48, 40.36, 29.62, 28.90, 28.77, 22.49, 21.26, 18.54

LRMS (ESI) m/z found 314.04 [M+Na]$^+$

Melting Point 92° C.

Example 7: Synthesis of Compound AM from Compound AL

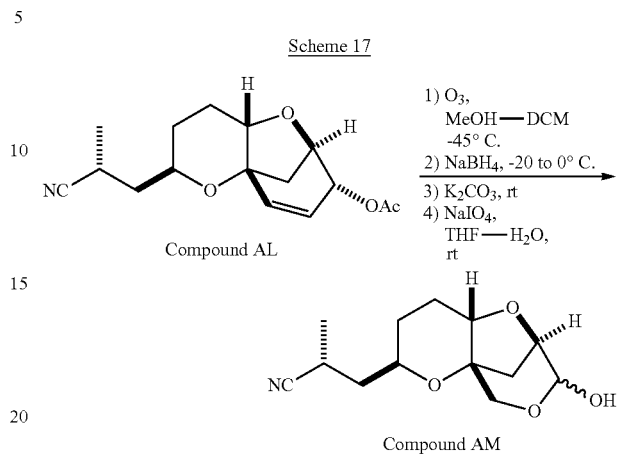

Scheme 17

Compound AL

1) O$_3$, MeOH—DCM -45° C.
2) NaBH$_4$, -20 to 0° C.
3) K$_2$CO$_3$, rt
4) NaIO$_4$, THF—H$_2$O, rt

Compound AM

Compound AL (1 Wt, 1 V, 1 eq) was dissolved in MeOH-DCM (5:3 v/v, 8.0 V) and cooled to -47° C. O$_3$ was bubbled into the mixture maintaining an internal temperature below -42° C. Upon complete consumption of Compound AL, excess O$_3$ was purged by N$_2$ bubbling until the peroxide test for the reactor outlet was negative.

The reaction mixture was then allowed to warm to -25° C. and NaBH$_4$ (0.0753 Wt, 0.580 eq) was added while maintaining an internal temperature below -17° C. Upon complete addition, the mixture was stirred at -20° C. for 1 hour and then allowed to warm to 0° C. NaBH$_4$ (granules, 0.0753 Wt, 0.580 eq) was added (while maintaining an internal temperature below 3° C.) and stirring was continued at 0° C. for one hour.

K$_2$CO$_3$ (0.712 Wt, 1.50 eq) was added at 0° C. and the reaction was allowed to warm to 20° C. Upon complete consumption of the acetate intermediate (approx 4 hours), the reaction mixture was cooled to 0° C. and 10 wt % HCl aq (5.1 Wt, 4.1 eq) was added under vigorous stirring to adjust the pH to 6-7.

The resultant biphasic mixture was partially concentrated (to approx 5.6 Wt) for removal volatiles, re-diluted with water-THF (1:1 v/v, 4.0 V), and cooled to 15° C. NaIO$_4$ (1.47 Wt, 2.00 eq) was added and the resultant slurry was stirred at 20° C. until complete consumption of triol (approx. 3 hours). The reaction mixture was then diluted with EtOAc (6.0 V), stirred vigorously for 5 minutes, and filtered through a pad of Celite (2 Wt). The filtrate (F-1) was separated and set aside and the filter cake was washed with EtOAc-EtOH (9:1 v/v, 4.0 V) (filtrate: F-2). NaCl (1.0 Wt) was added to F-1 and the resultant mixture was stirred vigorously for 5 minutes and allowed to partition. The organic layer was set aside and the aqueous layer was extracted with F-2. All of the organic layers were combined, sequentially washed with: 1) 10 wt % Na$_2$S$_2$O$_3$ aq (1.0 Wt); 2) water (1.0 V); 3) water (1.0 V) and concentrated to give a white solid. The residual water and solvents were azeotropically removed with EtOAc (6.0 V×3) to give the crude product as white solid (0.84 Wt, 0.96 eq). The crude was suspended in heptane-EtOAc (1:1 v/v, 3.5 V) and heated to 80° C. The resultant solution was cooled to room temperature over 2 hours (the precipitation started at ~65° C.). The mixture was further cooled to 0° C. and stirring was continued for an additional hour. The crystals were collected by filtration, washed with cold heptane-EtOAc (1:1 v/v, 1.8 V), and dried under $N_2$/vacuum to give Compound AM as white powder (0.58 Wt, 0.67 eq). The mother liquor was concentrated, suspended in heptane-EtOAc (4:3 v/v, 0.9 V), and heated to 80° C. The resultant clear solution was cooled to 20° C. over 2 hours. The mixture was further cooled to 0° C. and stirring was continued for an additional hour. The crystals were collected by filtration, washed with cold heptane-EtOAc (4:3 v/v, 0.50 V) and dried under $N_2$/vacuum to give additional Compound AM as white powder (0.068 Wt, 0.08 eq).

$^1$H NMR (for major anomer, 500 MHz, $CDCl_3$)

δ 4.96 (1H, s), 4.17 (1H, dd, J=6.0, 3.5 Hz), 3.90 (1h, d, J=9.5 Hz), 3.82-3.74 (2H, m), 3.41 (1H, dd, J=10, 3.0 Hz), 3.01 (1H, s), 2.95-2.85 (1H, m), 2.51-2.45 (1H, m), 2.22-2.15 (1H, m), 1.72-1.64 (1H, m), 1.63-1.48 (3H, m), 1.29 (3H, d, J=13 Hz), 1.30-1.18 (1H, m)

$^{13}$C NMR (for major anomer, 125 MHz, $CDCl_3$)

δ 122.81, 92.46, 77.17, 75.70, 72.43, 71.18, 68.36, 40.28, 29.82, 28.70, 28.40, 22.42, 18.52

LRMS (ESI) m/z found 307.99 $[M+MeOH+Na]^+$

Melting Point 116° C.

Example 8: Synthesis of Compound AN from Compound AM

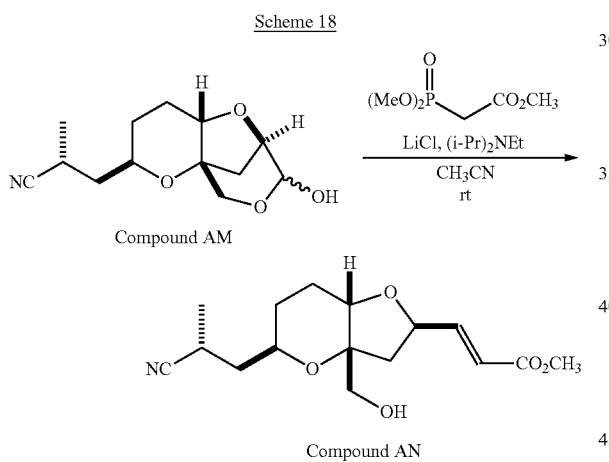

Compound AM (1 Wt, 1 V, 1 eq) was suspended in acetonitrile (4.0 V) and cooled to 10° C. LiCl (0.184 Wt, 1.10 eq) was added followed by N,N-diisopropylethylamine (0.825 V, 1.20 eq). After the internal temperature dropped to 10° C., trimethyl phosphonoacetate (0.703 V, 1.10 eq) was added at a rate such that the internal temperature did not exceed 13° C. Upon complete addition, the reaction was stirred at 10° C. for one hour and was then allowed to warm to 20° C. Stirring was continued at 20° C. until complete consumption of Compound AM. The reaction mixture was diluted with MTBE (8.0 V) and cooled to 0° C. 1.00 M HCl aq (5.0V, 1.5 eq) was added under vigorous stirring while maintaining the internal temperature below 8° C. and the resultant biphasic mixture was allowed to partition. The organic layer was set aside and the aqueous layer was extracted with MTBE (4.0 V & 2.0 V). All of the organic layers were combined, sequentially washed with: 1) 10 wt % $NaHCO_3$ aq (3.0 V); 2) water (2.0 V) and concentrated to give Compound AN as pale yellow oil (E:Z ~20:1).

$^1$H NMR (500 MHz, $CDCl_3$)

δ 6.87 (1H, dd, J=16.0, 3.5 Hz), 6.02 (1H, dd, J=16.0, 1.5 Hz), 4.81-4.86 (1H, m), 4.02 (1H, dd, J=9.0, 6.0 Hz), 3.86-3.91 (1H, m), 3.73 (3H, s), 3.46-3.52 (2H, m), 2.87-2.94 (1H, m), 2.51 (1H, dd, J=14.0, 10.0 Hz), 2.14 (1H, dd, J=7.5, 5.5 Hz), 1.92-1.98 (1H, m), 1.75-1.83 (1H, m), 1.66-1.74 (3H, m), 1.61-1.45 (1H, m), 1.33 (3H, d, J=7.0 Hz), 1.27-1.35 (1H, m)

$^{13}$C NMR (125 MHz, $CDCl_3$)

δ 166.95, 148.24, 123.08, 120.00, 84.03, 74.31, 74.25, 67.85, 67.77, 51.85, 40.23, 35.52, 26.80, 24.18, 22.27, 18.30

LRMS (ESI) m/z found 332.05 $[M+Na]^+$

Example 9: Synthesis of Compound AO from Compound AN

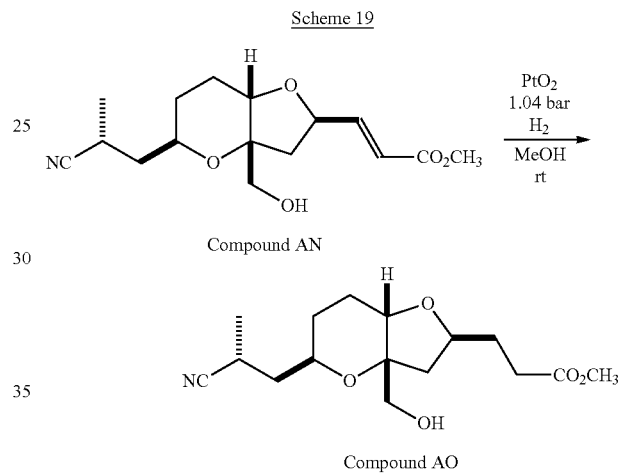

A reactor was charged with $PtO_2$ (0.73 wt %, 1.0 mol %) under an $N_2$ atmosphere. A solution of Compound AN in MeOH (10.0 V) was added under $N_2$. The resultant slurry was cooled to 15° C. and stirred under an atmosphere of 1.04 bar $H_2$. After two hours, the reaction was warmed to 20° C. and stirring was continued until complete consumption of Compound AN. The reaction mixture was filtered through a pad of celite (1 Wt) and the filter cake was washed with MeOH (5.0 V). The filtrate was concentrated and residual MeOH was azeotropically removed with anhydrous DCM (3.0 V×2) to give Compound AO as gray-colored oil (1.06 Wt, 1.05 eq). The crude product was used for next reaction without purification.

$^1$H NMR (500 MHz, $CDCl_3$)

δ 4.18-4.23 (1H, m), 3.82-3.91 (2H, m), 3.67 (3H, s), 3.53 (2H, d, J=6.5 Hz), 2.86-2.93 (1H, m), 2.40-2.46 (1H, m), 2.31-2.38 (2H, m), 2.17 (1H, t, J=7.0 Hz), 1.85-1.92 (1H, m), 1.59-1.84 (6H, m), 1.49 (1H, dd, J=14.0, 5.5 Hz), 1.32 (3H, d, J=7.5 Hz), 1.23-1.30 (1H, m)

$^{13}$C NMR (125 MHz, $CDCl_3$)

δ 173.90, 123.10, 84.23, 74.90, 73.28, 68.31, 67.73, 51.81, 40.28, 35.99, 31.75, 30.78, 27.12, 24.03, 22.27, 18.32

LRMS (ESI) m/z found 334.08 $[M+Na]^+$

Example 10: Synthesis of Compound AF from Compound AO

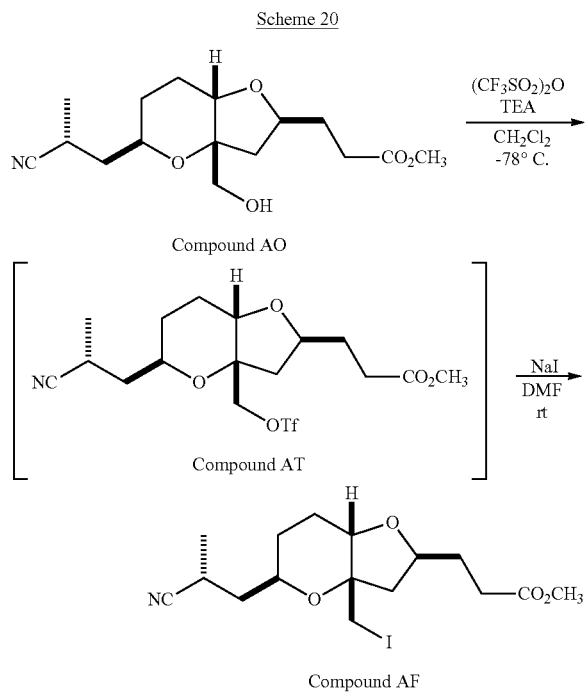

Scheme 20

Compound AO (1 Wt, 1 V, 1 eq) was dissolved in DCM (4.50 V). TEA (1.16 V, 0.84 Wt, 2.60 eq) was added and the mixture was cooled to −70° C. A solution of Tf$_2$O (0.702 V, 1.30 eq) in DCM (1.50 V) was added at a rate such that the internal temperature did not exceed −65° C. Upon complete addition, the reaction was stirred at −73° C. for 1.5 hours, allowed to warm to −20° C., and stirred at −20° C. for an additional 30 minutes.

DMF (3.0 V) was added and the mixture was allowed to warm to 0° C. NaI (0.674 Wt, 1.40 eq) was added and the reaction was further warmed to 23° C. Upon complete consumption of the triflate (Compound AT), the reaction mixture was diluted with heptane (8.0 V) and cooled to 0° C. Water (9.0 V) was added while maintaining an internal temperature below 10° C. The resultant biphasic mixture was stirred vigorously for 3 minutes and then allowed to partition. The organic layer was set aside and the aqueous layer was extracted with MTBE (6.0 V). All of the organic layers were combined, sequentially washed with: 1) 1.00 M HCl aq (5.00 V, 1.56 eq); 2) 10 wt % NaHCO$_3$ aq (2.0 V); 3) 10 wt % Na$_2$S$_2$O$_3$ aq (2.0 V), 4) water (2.0 V); 5) water (2.0 V) and concentrated. The residue was dissolved in MTBE (6.0 V) and silica gel (1.0 Wt) was added. The resultant slurry was stirred at 22° C. for 5 minutes and then filtered. The silica gel on the filter was washed with MTBE (8.0 V) and the filtrate was concentrated to give crude product as reddish solid (1.35 Wt, 1.00 eq).

Compound AF (1.35 Wt, 1.00 eq) was suspended in MTBE (1.4 V) and heated to 45° C. Heptane (2.8 V) was added while maintaining an internal temperature between 40° C. and 45° C. The resultant clear solution was cooled to 22° C. over 1 hour and then stirred at 22° C. for 2 hours. The mixture was cooled to 0° C. and stirring was continued for an additional 2 hours. The precipitations were collected by filtration, washed with pre-cooled (0° C.) heptane-MTBE (1:3 v/v, 2.8 V) and dried under N$_2$/vacuum for one hour to give Compound AF as light tan powder (0.98 Wt, 0.72 eq). The mother liquor was concentrated and re-dissolved in MTBE (0.33 V). Heptane (0.33 V) was added and the resultant clear solution was cooled to 0° C. A very small amount of Compound AF crystal (from the 1$^{st}$ crop) was added for seeding and stirring was continued at 0° C. for 15 hours. The precipitations were collected by filtration, washed with pre-cooled (0° C.) heptane-MTBE (1:2 v/v, 0.33 V), and dried under N$_2$/vacuum for 1 hour to give additional Compound AF as light tan powder (0.046 Wt, 0.034 eq).

Compound AT
$^1$H NMR (500 MHz, CDCl$_3$)
δ 4.46 (1H, d, J=10.5 Hz), 4.38 (1H, d, J=10.5 Hz), 4.21-4.26 (1H, m), 3.89 (1H, dd, J=8.5, 6.0 Hz), 3.81-3.86 (1H, m), 3.68 (3H, s), 2.93-3.00 (1H, m), 2.41-2.50 (2H, m), 2.33-2.39 (1H, m), 1.91-1.97 (1H, m), 1.64-1.92 (6H, m), 1.45 (1H, dd, J=14.5, 5.5 Hz), 1.25-1.35 (1H, m), 1.32 (3H, d, J=7.0 Hz)
$^{13}$C NMR (125 MHz, CDCl$_3$)
δ 173.62, 122.86, 117.51, 81.84, 78.54, 74.57, 73.08, 68.63, 51.94, 40.16, 35.28, 31.77, 30.64, 27.13, 23.95, 22.33, 18.42
LRMS (ESI) m/z found 446.12 [M+Na]$^+$ Compound AF
$^1$H NMR (500 MHz, CDCl$_3$)
δ 4.21-4.26 (1H, m), 3.78-3.83 (2H, m), 3.67 (3H, s), 3.44 (1H, d, J=10.0 Hz), 3.37 (1H, d, J=10.0 Hz), 2.99-3.03 (1H, m), 2.49 (1H, dd, J=9.0, 8.5 Hz), 2.42-2.47 (1H, m), 2.32-2.38 (1H, m), 1.80-1.89 (3H, m), 1.63-1.75 (5H, m), 1.33 (3H, d, J=7.5 Hz), 1.24-1.30 (1H, m)
$^{13}$C NMR (125 MHz, CDCl$_3$)
δ 173.74, 122.89, 81.75, 76.07, 75.10, 68.24, 51.86, 40.52, 39.00, 31.78, 30.75, 27.09, 24.36, 22.53, 18.72, 18.51
LRMS (ESI) m/z found 444.02 [M+Na]$^+$
Melting Point 69.5° C.

Example 11: Synthesis of Compound AP from Compound AF

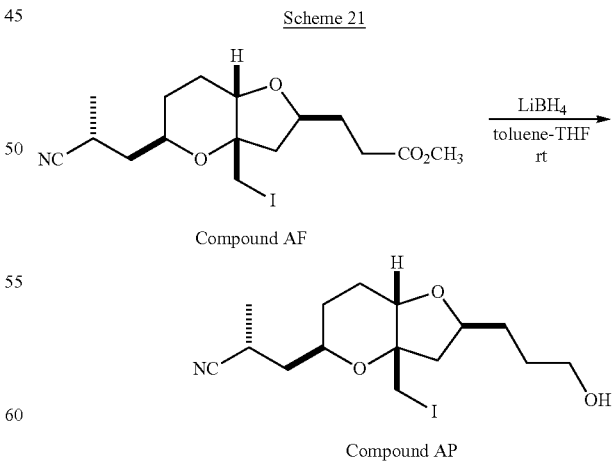

Scheme 21

Compound AF (1 Wt, 1 V, 1 eq) was dissolved in toluene (5.0 V) and cooled to 10° C. LiBH$_4$ (2.0 M solution in THF, 2.4 V, 2.0 eq) was added and stirring was continued at 20° C. for 18 hours. The reaction mixture was cooled to 0° C.

and slowly poured into a pre-cooled (0° C.) mixture of EtOAc (6 V) and 1.0 M HCl aq (6.0 V, 2.5 eq) under vigorous stirring. The reactor was rinsed with EtOAc (2 V) and the resultant wash was combined with the biphasic mixture. The organic layer was set aside and the aqueous layer was extracted with EtOAc (5.0 V). All of the organic layers were combined, sequentially washed with: 1) 10 wt % NaHCO$_3$ aq (2 V); 2) water (2 V) and concentrated. The residual water was azeotropically removed with toluene (5 V×2) to give Compound AP (0.93 Wt, 0.89 eq).

$^1$H NMR (500 MHz, CDCl$_3$)

δ 4.24-4.30 (1H, m), 3.86 (1H, dd, J=8.5, 6.0 Hz), 3.78-3.83 (1H, m), 3.62-3.68 (2H, m), 3.44 (1H, d, J=10.5 Hz), 3.38 (1H, d, J=10.5 Hz), 2.99-3.04 (1H, m), 2.51 (1H, dd, J=14.0, 8.5 Hz), 2.06 (1H, t, J=6.0 Hz), 1.86-1.92 (1H, m), 1.59-1.78 (9H, m), 1.33 (3H, d, J=7.0 Hz), 1.24-1.31 (1H, m)

$^{13}$C NMR (125 MHz, CDCl$_3$)

δ 122.94, 82.70, 76.27, 76.25, 68.42, 62.77, 40.50, 39.08, 33.72, 29.67, 27.25, 24.59, 22.55, 19.08, 18.51

LRMS (ESI) m/z found 416.02 [M+Na]$^+$

Example 12: Synthesis of Compound AU from Compound AP

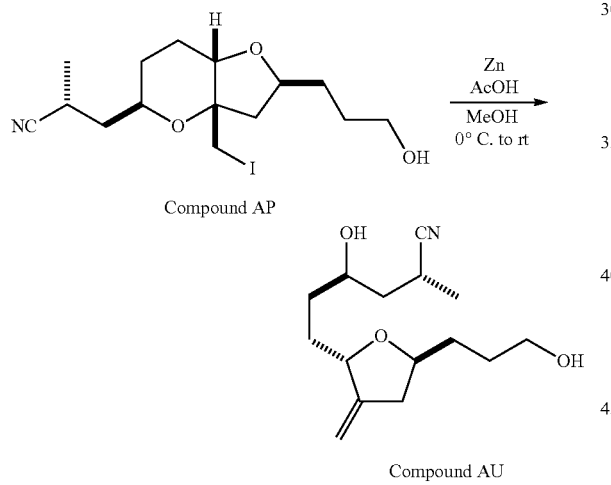

An inert reactor was charged with Zn powder (2.5 Wt, 15 eq) at 23° C. MeOH (5.0 V) was added followed by AcOH (2.0 V, 14 eq). The resultant slurry was stirred at 23° C. for 20 minutes and then cooled to 0° C. A solution of Compound AP (1 Wt, 1 V, 1 eq) in MeOH (5.0 V) was added and vigorous stirring was continued at 0° C. for 3 hours and at 23° C. for 1.5 hours. The reaction mixture was diluted with EtOAc (20 V). Excess Zn powder was removed by filtration and rinsed with EtOAc (10 V). The filtrate was washed with 1.00 M HCl aq (10 V). The organic layer was set aside and the aqueous layer was extracted with EtOAc (20 V). All of the organic layers were combined, sequentially washed with: 1) 10 wt % NaHCO$_3$ aq (20 V); 2) 10 wt % Na$_2$S$_2$O$_3$ aq (8 V); 3) brine (8 V), and concentrated to give the crude product as pale yellow oil. The crude was purified by flash column chromatography (Biotage, heptane-EtOAc 3:7→2:8→0:10) to give Compound AU (0.62 Wt, 0.90 eq) as pale yellow oil.

$^1$H NMR (500 MHz, CDCl$_3$)

δ 5.01 (1H, s), 4.85 (1H, s), 4.41 (1H, br), 4.08-4.12 (1H, m), 3.93 (1H, br), 3.60-3.68 (2H, m), 3.12 (1H, br), 2.97-3.05 (1H, m), 2.69-2.73 (1H, m), 2.45 (1H, br), 2.29-2.33 (1H, m), 1.53-1.80 (10H, m), 1.33 (3H, d, J=7.5 Hz)

$^{13}$C NMR (125 MHz, CDCl$_3$)

δ 150.95, 123.29, 105.49, 79.66, 77.69, 68.79, 62.84, 41.83, 39.03, 34.33, 32.11, 30.89, 29.80, 22.93, 18.61

LRMS (ESI) m/z found 289.96 [M+Na]$^+$

Example 13: Synthesis of Compound AR from Compound AU

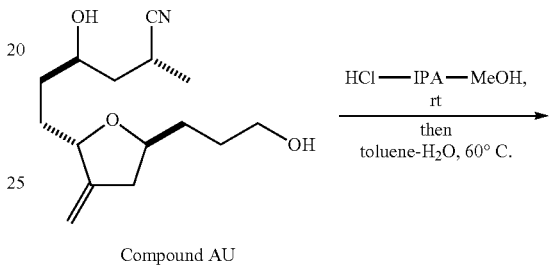

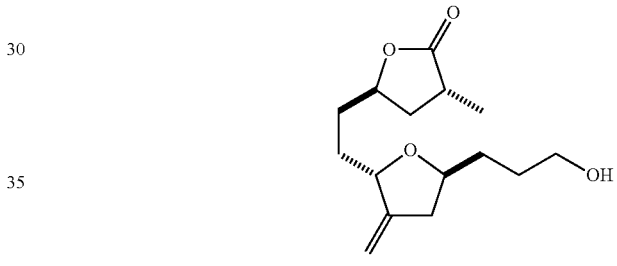

Compound AU (1 Wt, 1 V, 1 eq) was dissolved in MeOH (2.0 V). The mixture was cooled to 0° C. and HCl (6 M solution in IPA, 2.0 V, 13 eq) was added. The reaction was allowed to warm to 23° C. and stirring was continued until complete consumption of Compound AU (approx. 20 hours). The reaction mixture was diluted with toluene (8.0 V) and water (4.0 V) and the resultant biphasic mixture was heated at 60° C. for 3 hours. After cooling down, organic layer was set aside and aqueous layer was extracted with EtOAc (8.0 V). All organic layers were combined, sequentially washed with: 1) 10 wt % NaHCO$_3$ aq (2.0 V); 2) brine (2.0 V); 3) water (2.0 V), and concentrated to give crude Compound AR (0.93 Wt, 0.93 eq) as pale yellow oil. The crude product was azeotropically dried with toluene (8 V×2) and used for next reaction without purification.

$^1$H NMR (500 MHz, CDCl$_3$)

δ 4.98-4.99 (1H, m), 4.84-4.85 (1H, m), 4.49-4.54 (1H, m), 4.39 (1H, d, J=10.5 Hz), 4.00-4.05 (1H, m), 3.59-3.68 (2H, m), 2.63-2.72 (2H, m), 2.56-2.62 (1H, m), 2.25-2.30 (1H, m), 2.08-2.14 (1H, m), 1.97-2.02 (1H, m), 1.52-1.82 (7H, m), 1.26 (3H, d, J=7.5 Hz), 1.24-1.34 (1H, m)

$^{13}$C NMR (125 MHz, CDCl$_3$)

δ 180.34, 151.14, 105.39, 79.71, 78.84, 77.54, 62.72, 39.02, 35.69, 34.15, 32.19, 32.16, 31.50, 29.64, 16.02

LRMS (ESI) m/z found 290.99 [M+Na]$^+$

Example 14: Synthesis of Compound AH from Compound AR

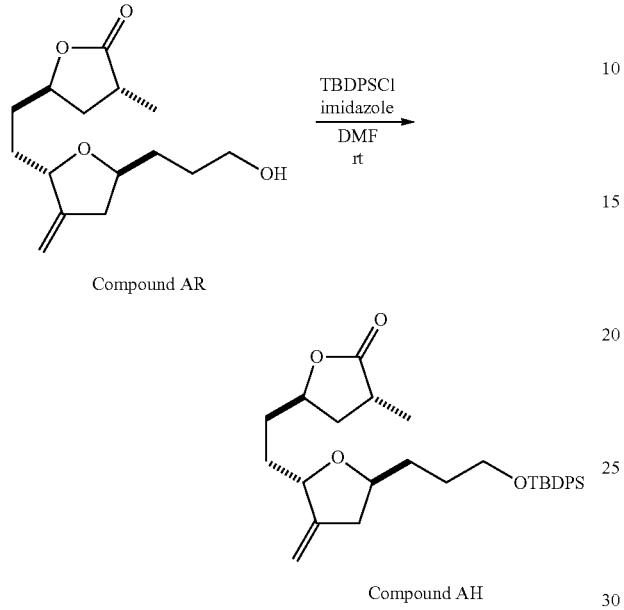

Example 15: Synthesis of Compound AV from Compound AH

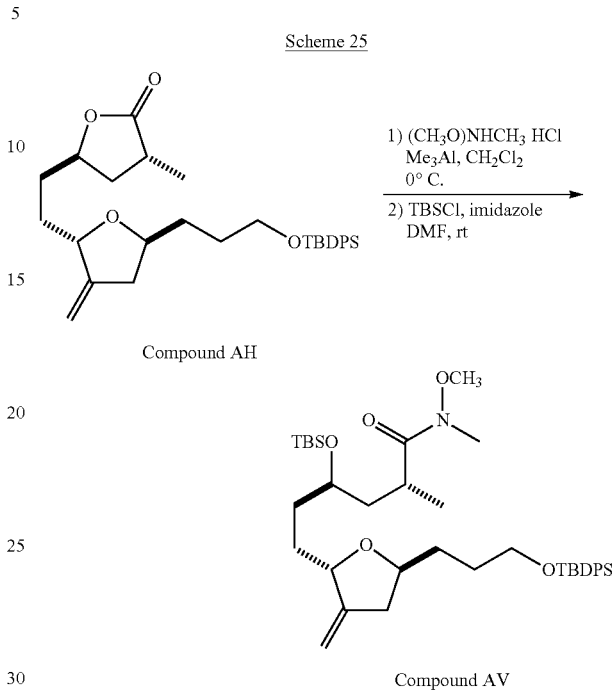

Compound AR (1 Wt, 1 V, 1 eq) was dissolved in DMF (2.0 vols) and imidazole (0.330 Wt, 1.30 eq) was added at 23° C. (endothermic). Upon complete dissolution of imidazole, the mixture was cooled to 10° C. and tert-butylchlorodiphenylsilane (TBDPSCl, 0.969 V, 1.02 Wt, 1.00 eq) was added. The reaction mixture was stirred at 10° C. for 1 hour, allowed to warm to 23° C., and stirred until complete consumption of Compound AR (approx. 3 hours). The reaction mixture was diluted with Heptane-MTBE 1:1 (8.0 V) and cooled to 10° C. Water (8.0 V) was added under vigorous stirring and the resultant mixture was allowed to partition. The aqueous layer was set aside. The organic layer was further washed with water (1.0 V) and concentrated. Residual water and solvents were azeotropically removed with toluene (8.0 V×2) to give Compound AH as colorless oil (1.98 Wt, 100%). The crude product was used for next reaction without purification $^1$H NMR (500 MHz, CDCl$_3$)

δ 7.65-7.67 (4H, m), 7.36-7.44 (6H, m), 4.99 (1H, dd, J=4.0, 2.5 Hz), 4.84 (1H, dd, J=4.0, 2.5 Hz), 4.50-4.55 (1H, m), 4.35 (1H, d, J=9.0 Hz), 3.97-4.02 (1H, m), 3.66-3.70 (2H, m), 2.66-2.71 (1H, m), 2.61-2.66 (1H, m), 2.22-2.27 (1H, m), 2.08-2.14 (1H, m), 1.97-2.03 (1H, m), 1.50-1.81 (8H, m), 1.28 (3H, d, J=7.5 Hz), 1.04 (9H, s)

$^{13}$C NMR (125 MHz, CDCl$_3$)

δ 180.18, 151.68, 135.79 (4C), 134.21 (2C), 129.84 (2C), 127.89 (4C), 105.27, 79.58, 78.83, 77.38, 64.02, 39.08, 35.78, 34.20, 32.29, 31.76, 31.60, 29.31, 27.16 (3C), 19.48, 16.15

LRMS (ESI) m/z found 529.26 [M+Na]$^+$

An inert reactor was charged with N,O-Dimethylhydroxylamine hydrochloride (0.298 Wt, 1.55 eq). DCM (2.0 V) was added and the resultant slurry was cooled to −5° C. Trimethylaluminum (2.0 M solution in toluene, 1.48 V, 1.50 eq) was slowly added at a rate such that the internal temperature did not exceed 3° C. Upon complete addition, the mixture was stirred at 0° C. for 30 minutes. A solution of Compound AH (1 Wt, 1 V, 1 eq) in DCM (3.0 V) was added at a rate such that the internal temperature did not exceed 5° C. and stirring was continued at 0° C. until complete consumption of Compound AH. Another reactor was charged with 20 wt % Rochelle salt (10 Wt) and MTBE (10 V), and cooled to 0° C. The reaction mixture was transferred into the pre-cooled biphasic mixture while maintaining the internal temperature below 5° C. The resultant mixture was vigorously stirred at 0° C. for 30 minutes and then allowed to partition. The organic layer was set aside and the aqueous layer was extracted with MTBE (10 V). All of the organic layers were combined, sequentially washed with: 1) 20 wt % Rochelle salt solution (5 Wt); 2) water (3 V); 3) brine (2 V), and concentrated to give the crude product as pale yellow oil. The crude product was azeotropically dried with toluene (5 V×2) and used for the following reaction without purification.

The crude hydroxyamide was dissolved in DMF (2.0 V) and cooled to 10° C. Imidazole (0.161 Wt, 1.20 eq) was added followed by TBSCl (0.297 Wt, 1.00 eq). The reaction was stirred at 15° C. for 2 hours, allowed to warm to 23° C., and stirred until complete consumption of the hydroxyamide intermediate. The reaction mixture was diluted with heptane-MTBE 1:1 (10 V) and cooled to 0° C. Water (8 V) was added and the resultant biphasic mixture was vigorously stirred and allowed to partition. The organic layer was set aside and aqueous layer was extracted with heptane-MTBE (1:1 v/v, 8.0 V). All of the organic layers were combined, sequentially washed with: 1) water (3.0 V); 2) brine (3.0 V), and concentrated to give crude Compound AV (1.35 Wt, 0.99 eq) as a pale yellow oil.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A compound of formula (I):

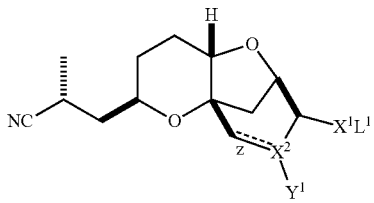

(I)

wherein:
z is a single or double bond, provided that when z is a double bond, $X^2$ is C and $Y^1$ is hydrogen; and provided that when z is a single bond, $X^2$ is CH or O;
$X^1$ is O, S, or CN, provided that when $X^1$ is CN or S, $X^2$ is O;
$Y^1$ is a halide, hydrogen or O-$L^2$, or absent when $X^2$ is O; and
$L^1$ and $L^2$ are independently selected from hydrogen and a protecting group independently selected from the group consisting of $C_1$-$C_{12}$ alkylcarbonyl, $C_1$-$C_6$ alkyl, aryl ($C_1$-$C_6$) alkyl, silyl ($C_1$-$C_{10}$), carbonate, $C_1$-$C_6$ alkoxy-($C_1$-$C_6$) alkyl, 3,4-dimethoxybenzyl, p-methoxybenzyl, and $C_1$-$C_6$ ester, or $L^1$ and $L^2$ together are a protecting group selected from the group consisting of pyran, cyclic $C_1$-$C_6$ acetal, cyclic $C_3$-$C_7$ ketal, and cyclic carbonate, provided that when $X^1$ is CN, $L^1$ is absent; or a salt thereof.

2. The compound of claim 1, wherein at least one of $L^1$ and $L^2$ is a protecting group selected from the group consisting of methoxymethyl, trimethylsilyl, triethylsilyl, t-butyldimethylsilyl, t-butyldiphenylsilyl, triisopropylsilyl, methyl, t-butyl, 3,4-dimethoxybenzyl, p-methoxybenzyl, benzyl, and trityl, or $L^1$ and $L^2$ together are cycloheptylidine.

3. The compound of claim 1, wherein at least one of $L^1$ and $L^2$ is $C_1$ alkyl carbonyl, or $L^1$ and $L^2$ together are acetonide, benzylidene, cyclohexylidene, or cyclopentylidene.

4. The compound of claim 1 having formula (Ib):

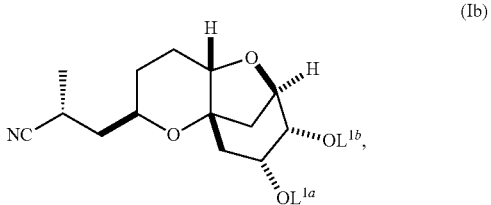

(Ib)

wherein $L^{1a}$ and $L^{1b}$ are independently selected from hydrogen and a protecting group, selected from the group consisting of $C_1$-$C_6$ alkyl, aryl ($C_1$-$C_6$) alkyl, silyl ($C_1$-$C_{10}$), and $C_1$-$C_6$ ester, or $L^{1a}$ and $L^{1b}$ together are a divalent protecting group selected from the group consisting of cyclic $C_1$-$C_6$ acetal, cyclic $C_3$-$C_7$ ketal, and cyclic carbonate.

* * * * *